(12) United States Patent
Elanany et al.

(10) Patent No.: US 10,723,630 B2
(45) Date of Patent: Jul. 28, 2020

(54) METHODS OF PRODUCING COMPOSITE ZEOLITE CATALYSTS FOR HEAVY REFORMATE CONVERSION INTO XYLENES

(71) Applicants: Saudi Arabian Oil Company, Dhahran (SA); Universitat Politecnica De Valencia, Valencia (ES); Consejo Superior De Investigaciones Cientificas, Madrid (ES)

(72) Inventors: Mohamed Elanany, Ras Tanura (SA); Raed Abudawoud, Al-Khobar (SA); Avelino Corma Canos, Valencia (ES); M. Teresa Portilla Ovejero, Valencia (ES); Vicente J. Margarit Benavent, Valencia (ES); M. Teresa Navarro Villalba, Valencia (ES); M. Cristina Martinez Sanchez, Valencia (ES); Ibrahim M. Al-Zahrani, Dammam (SA); Khalid A. Al-Majnouni, Riyadh (SA)

(73) Assignees: Saudi Arabian Oil Company, Dhahran (SA); Universitat Politecnica De Valencia, Valencia (ES); Consejo Superior De Investigaciones Cientificas, Madrid (ES)

( * ) Notice: Subject to any disclaimer, the term of this patent is extended or adjusted under 35 U.S.C. 154(b) by 0 days.

(21) Appl. No.: 16/299,832

(22) Filed: Mar. 12, 2019

(65) Prior Publication Data

US 2019/0284056 A1 Sep. 19, 2019

(30) Foreign Application Priority Data

Mar. 14, 2018 (EP) .................................. 18382167

(51) Int. Cl.
*C01B 39/02* (2006.01)
*B01J 29/48* (2006.01)
(Continued)

(52) U.S. Cl.
CPC ............. *C01B 39/023* (2013.01); *B01J 29/40* (2013.01); *B01J 29/44* (2013.01); *B01J 29/46* (2013.01);
(Continued)

(58) Field of Classification Search
CPC ....... C01B 39/023; C01B 39/38; C01B 39/48; C01P 2002/72; C07C 15/08;
(Continued)

(56) References Cited

U.S. PATENT DOCUMENTS 4,467,129 A 8/1984 Iwayama et al.
4,963,337 A 10/1990 Zones
(Continued)

FOREIGN PATENT DOCUMENTS

CN 101121132 A 2/2008
CN 101121137 A 2/2008
(Continued)

OTHER PUBLICATIONS

International Search Report and Written Opinion dated Sep. 20, 2019 pertaining to International application No. PCT/US2019/021594 filed Mar. 11, 2019.
(Continued)

*Primary Examiner* — David M Brunsman
(74) *Attorney, Agent, or Firm* — Dinsmore & Shohl LLP

(57) ABSTRACT

A method of forming a composite zeolite catalyst includes combining a silicon source and an aqueous organic structure directing agent having a polyamino cation compound to form a silica intermediary gel, introducing an aluminum precursor to the silica intermediary gel to form a catalyst
(Continued)

precursor gel, evaporating water in the catalyst precursor gel to form a catalyst gel, and heating the catalyst gel to form a composite zeolite catalyst particle having an intergrowth region with a mixture of both Beta crystals and ZSM-5 crystals. An associated method of making xylene includes feeding heavy reformate to a reactor, the reactor containing the composite zeolite catalyst, and producing xylene by simultaneously performing dealkylation and transalkylation of the heavy reformate in the reactor, where each composite zeolite catalyst particle is able to catalyze both the dealkylation and transalkylation reactions.

15 Claims, 13 Drawing Sheets

(51) Int. Cl.

| | | |
|---|---|---|
| C07C 15/08 | (2006.01) | |
| B01J 29/78 | (2006.01) | |
| B01J 35/10 | (2006.01) | |
| C01B 39/04 | (2006.01) | |
| C01B 39/38 | (2006.01) | |
| C01B 39/48 | (2006.01) | |
| C07C 4/18 | (2006.01) | |
| C07C 6/12 | (2006.01) | |
| B01J 29/46 | (2006.01) | |
| B01J 29/80 | (2006.01) | |
| B01J 29/44 | (2006.01) | |
| B01J 35/00 | (2006.01) | |
| B01J 29/76 | (2006.01) | |
| B01J 29/74 | (2006.01) | |
| B01J 29/40 | (2006.01) | |
| B01J 29/70 | (2006.01) | |
| B01J 29/06 | (2006.01) | |

(52) U.S. Cl.
CPC ............ *B01J 29/48* (2013.01); *B01J 29/7007* (2013.01); *B01J 29/7415* (2013.01); *B01J 29/7615* (2013.01); *B01J 29/7815* (2013.01); *B01J 29/80* (2013.01); *B01J 35/002* (2013.01); *B01J 35/1019* (2013.01); *B01J 35/1023* (2013.01); *C01B 39/04* (2013.01); *C01B 39/38* (2013.01); *C01B 39/48* (2013.01); *C07C 4/18* (2013.01); *C07C 6/126* (2013.01); *B01J 2029/062* (2013.01); *B01J 2229/62* (2013.01); *B01J 2231/646* (2013.01); *C01P 2002/72* (2013.01); *C07C 15/08* (2013.01); *C07C 2529/46* (2013.01); *C07C 2529/48* (2013.01); *C07C 2529/78* (2013.01); *C07C 2529/80* (2013.01)

(58) Field of Classification Search
CPC ....... C07C 2529/80; B01J 29/40; B01J 29/44; B01J 29/48; B01J 29/7007; B01J 29/7415; B01J 29/7615; B01J 29/7815; B01J 29/80; B01J 2029/062; B01J 2231/646

See application file for complete search history.

(56) References Cited

U.S. PATENT DOCUMENTS

| | | | |
|---|---|---|---|
| 5,043,513 A | 8/1991 | Howley et al. | |
| 5,120,425 A | 6/1992 | Zones et al. | |
| 5,865,986 A | 2/1999 | Buchanan et al. | |
| 5,942,651 A | 8/1999 | Beech, Jr. et al. | |
| 5,952,536 A | 9/1999 | Nacamuli et al. | |
| 7,393,989 B2 | 7/2008 | Negiz et al. | |
| 8,242,321 B2 | 8/2012 | Boldingh et al. | |
| 8,329,973 B2 | 12/2012 | Inui et al. | |
| 8,653,315 B2 | 2/2014 | Ali | |
| 9,242,236 B2* | 1/2016 | Xie | B01J 29/80 |
| 2002/0092797 A1 | 7/2002 | Choi et al. | |
| 2005/0234279 A1* | 10/2005 | Serra | B01J 29/80 585/475 |
| 2009/0023968 A1* | 1/2009 | Wang | B01J 29/068 585/323 |
| 2009/0112034 A1 | 4/2009 | Levin | |
| 2009/0325785 A1 | 12/2009 | Moscoso et al. | |
| 2010/0029467 A1 | 2/2010 | Inui et al. | |
| 2011/0127193 A1 | 6/2011 | Xie et al. | |
| 2012/0083635 A1 | 4/2012 | Boldingh et al. | |
| 2012/0165558 A1 | 6/2012 | Ryoo et al. | |
| 2012/0258852 A1 | 10/2012 | Martinez et al. | |
| 2013/0261365 A1 | 10/2013 | Wang et al. | |
| 2013/0281750 A1 | 10/2013 | Abudawoud | |
| 2018/0134637 A1 | 5/2018 | Lai et al. | |

FOREIGN PATENT DOCUMENTS

| | | | |
|---|---|---|---|
| CN | 101190418 A | | 6/2008 |
| CN | 101190864 A | * | 6/2008 |
| CN | 101191069 A | * | 6/2008 |
| CN | 101347746 A | * | 1/2009 |
| CN | 101348407 A | * | 1/2009 |
| CN | 101602639 A | * | 12/2009 |
| CN | 101885663 A | | 11/2010 |
| CN | 101811063 B | | 10/2012 |
| CN | 104437611 A | | 3/2015 |
| CN | 104437613 A | * | 3/2015 |
| EP | 042754 A1 | | 6/1981 |
| EP | 109962 A1 | | 6/1984 |
| EP | 1586376 A1 | | 10/2005 |
| EP | 1775277 A1 | | 4/2007 |
| WO | 2004046278 A1 | | 6/2004 |
| WO | 2005118515 A1 | | 12/2005 |
| WO | 2010150996 A2 | | 12/2010 |
| WO | 2018011122 A1 | | 1/2018 |
| WO | 2018071184 A1 | | 4/2018 |
| WO | 2018231340 A1 | | 12/2018 |

OTHER PUBLICATIONS

Ali et al., "Selective production of xylenes from alkyl-aromatics and heavy reformates over dual-zeolite catalyst", Catalysis Today, vol. 243, pp. 118-127 (2015).

Al-Khattaf et al., "Catalytic transformation of methyl benzenes over zeolite catalysts", Applied Catalysis A: General 394, pp. 176-190, 2011.

Calderia et al., "Properties of hierarchical Beta zeolites prepared from protozeolitic nanounits for the catalytic cracking of high density polyethylene", Applied Catalysts A: General 531, pp. 187-196, 2017.

Choi et al., "Stable single-unit-cell nanosheets of zeolite MFI as active and long-lived catalysts", Nature, vol. 461, pp. 246-250, Sep. 10, 2009.

Corma et al., "Discovery of new paraffin isomerization catalysts based on SO4 2—/ZrO2 and WoxlZrO2 applying combinatorial techniques", Catalysts Today 81, pp. 495-506, 2003.

Han et al., Zeolite Synthesis Using Flexible Diquartemary Alkylammonium Ions (CnH2n+1)2HN+(CH2)5N+H(CnH2n+1)2 with n=1-5 as Structure-Directing Agents, Chem Mater, vol. 17, pp. 477-486, 2005.

Jackowski et al., "Diquatemary Ammonium Compounds in Zeolite Synthesis: Cyclic and Polycyclic N-Heterocycles Connected by Methylene Chains", American Chemical Society, 131, 1092-1100 (2009).

Jo et al., "Capping with Multivalent Surfactants for Zeolite Nanocrystal Synthesis", Angew. Chem, vol. 125, pp. 10198-10201, 2013 with Supporting Information.

Kim et al., "Bulk crystal seeding on generation of mesoporoes by organosilane surfactants in zeolite synthesis", Electronic Supplementary (ESI) for Journal of Masterials Chemistry A., The Royal Society of Chemistry 2014.

(56) References Cited

OTHER PUBLICATIONS

Kong et al., "Fabrication of core/shell structure via overgrowth of ZSM-5 layers on mordenite cyrstals", Microporous and Mesoporous Materials, vol. 119, pp. 91-96, 2009.
Konysheva et al., "Effect of Nature of Heteroelement (Ba, Ga, Al) on Adsorption of Acid Characteristics of Hierarchical Porous Zeolites of MOR, BEA and MTW Strucural Types", Theoretical and Experimental Chemistry, vol. 53, No. 6, pp. 410-416, Jan. 2018.
Va Laak et al., "Mesoporous mordenites obtained by sequential acid and alkaline treatments—Catalysts for cumene production with enhanced accessibility", Journal of Catalysis, vol. 276, pp. 170-180, 2010.
Lee et al., "Reinvestigation into the synthesis of zeolites using diquaternary alkylammonium ions (CH3)3N+(CH2)nNf(CH3)3 with n=3-10 as structure-directing agents", Microporous and Mesoporous Materials, vol. 68, pp. 97-104, 2004.
Lee et al., "Zeolite synthesis in the presence of flexible diquaternary alkylammonium ions (C2H5)3N+(CH2)nN+(C2H5)3 with n+3-10 as structure-directing agents", Microporous and Mesoporous Materials, vol. 60, pp. 237-249, 2003.
Li et al., "One-pot synthesis of hierarchical mordenite and its performance in the benzylation of benzene with benzyl alcohol", J. Matter Sci, vol. 50, pp. 5059-5067, 2015.
Mihayli et al., "Transformation of ethylbenzene-m-xylene misture on zeolites with different structures", J. Porous Matter, vol. 21, pp. 485-493, 2014.
Liu et al., "Catalytic Properties of Hierarchical Mordenite Nanosheets Synthesized by Self-Assembly Between Subnanocrystals and Organic Templates", Catal Lett, vol. 146, pp. 249-254, 2016 with Electronic Supplementary Information.
Moller et al., "Mesoporosity—a new dimension for Zeolites", Chem Soc Rev. vol. 42, pp. 3689-3707, 2013.
Ordomsky et al., "Cumene disproportionation over micro/mesoprous catalysts obtained by recrystallization of mordenite", Journal of Catalysis, vol. 295, pp. 207-216, 2012.
Shvets et al., "New Approaches to Creation of Micro- and Mesoporous Functional Materials", Theoretical and Experimental Chemiustry, vol. 53, No. 5, Nov. 2017.
Thommes et al., "Physisorption of gases, with special reference to the evaluation of surface area and pore size dstribution (IUPAC Technical Report)", Pure Appl. Chem., 87(9-10), pp. 1051-1069, 2015.
Verboekend et al., "Design of hierarchical zeolite catalysts by desilication", Catalysis Science & Technology, vol. 1, pp. 879-890, 2011.
Vitvarova et al., "Catalytic applications and FTIR investigation of zeolite SSZ-33 after isomorphous substitution", Microporous and Mesoporous Materials, vol. 194, pp. 174-182, 2014.
Zones et al., "Boron-beta zeolite hydrothermal conversions: the influence of template structure and of boron concentration and source", Microporous Materials, vol. 2, pp. 543-555, 1994.
European Search Report pertaining to European Application No. 18382172.7 dated Jan. 4, 2019.
European Search Report pertaining to European Application No. 18382170.1 dated Sep. 27, 2018.
European Search Report pertaining to European Application No. 18382168.5 dated Sep. 27, 2018.
European Search Report pertaining to European Application No. 18382167.7 dated Jan. 4, 2019.
European Search Report pertaining to European Application No. 18382169.3 dated Sep. 27, 2018.
European Search Report pertaining to European Application No. 18382171.9 dated Oct. 5, 2018.
Galarneau et al., Validity of the t-plot Method to Assess Microporosity in Hierarchical Micro/Mesoporous Materials, Langmuir 2014, 9 pgs.
International Search Report and Written Opinion dated Jun. 27, 2019 pertaining to International application No. PCT/US2019/021592 filed Mar. 11, 2019, 15 pgs.
International Search Report and Written Opinion dated Jun. 28, 2019 pertaining to International application No. PCT/US2019/021597 filed Mar. 11, 2019, 17 pgs.
International Search Report and Written Opinion dated Jun. 26, 2019 pertaining to International application No. PCT/US2019/021590 filed Mar. 11, 2019, 23 pgs.
International Search Report and Written Opinion dated Jun. 26, 2019 pertaining to International application No. PCT/US2019/021595 filed Mar. 11, 2019, 20 pgs.
Office Action dated Dec. 2, 2019 pertaining to U.S. Appl. No. 16/299,717, filed Mar. 12, 2019, 26 pgs.
Office Action dated Dec. 4, 2019 pertaining to U.S. Appl. No. 16/299,723, filed Mar. 12, 2019, 30 pgs.
Office Action dated Dec. 20, 2019 pertaining to U.S. Appl. No. 16/299,838 filed Mar. 12, 2019, 30 pgs.
Office Action dated Dec. 20, 2019 pertaining to U.S. Appl. No. 16/299,844, filed Mar. 12, 2019, 31 pgs.
Machine translation CN 101811063, dated Aug. 25, 2010, retrieved Dec. 6, 2019 (Year: 2019).
Camblor et al. "Characterization of Nanocrystalline Zeolite Beta" Microporous and Mesoporous Materials 25 (1998) pp. 59-74 (Year: 1998).

* cited by examiner

METHODS OF PRODUCING COMPOSITE ZEOLITE CATALYSTS FOR HEAVY REFORMATE CONVERSION INTO XYLENES

CROSS REFERENCE TO RELATED APPLICATIONS

This application claims priority to European Application No. 18382167.7, filed Mar. 14, 2018 which is hereby incorporated by reference in its entirety.

TECHNICAL FIELD

Embodiments of the present specification generally relate to catalysts, and specifically relate to forming composite zeolite catalysts and methods of using the same.

BACKGROUND

Heavy reformate (HR), containing mainly $C_{9+}$ aromatics, is the fraction that remains after extraction of the more valuable BTEX (benzene, toluene, ethylbenzene, xylene) fraction from the catalytic reformate or the pyrolysis gasoline. Traditionally this fraction was directly added to the gasoline pool. However, due to the restriction of the benzene content in gasoline by environmental regulations, it is important to find alternative ways of upgrading this stream into other valuable products. One option is to convert the heavy aromatics in the heavy reformate into xylenes. Demand is growing faster for xylene derivatives than for benzene derivatives. Therefore, a higher yield of xylenes at the expense of benzene yield is a favorable objective. Heavy reformate may be converted into xylenes and other compounds by means of dealkylation of the $C_{9+}$ alkylaromatics or by transalkylation of these compounds with benzene or toluene.

Heavy reformate may also be converted into xylenes by dealkylation of the $C_{9+}$ alkylaromatics to benzene and toluene, and further transalkylation of these compounds formed by dealkylation with other $C_{9+}$ alkylaromatics present in the feed. Regardless, these means to produce xylenes by simultaneous dealkylation and transalkylation have limited efficiency, because of the sequential nature of the conversion reaction process where products of a first reaction are utilized in a second reaction.

SUMMARY

Accordingly, ongoing needs exist for catalysts suitable for efficiently converting heavy reformates to produce xylenes. Embodiments of the present disclosure are related to composite zeolite catalysts, their preparation methods and performance, particularly to the synthesis of such catalysts having intimate contact at the nanocrystal level between the zeolite constituents. The zeolite composite catalysts may convert a mixture of heavy aromatic compounds (such as those present in heavy reformate), particularly $C_9$ aromatic hydrocarbons to benzene, toluene, and xylenes, and particularly to commercially valuable xylenes. The conversion reactions include dealkylation, transalkylation, and disproportionation. The zeolite composite catalysts have a high ethyl-dealkylation activity as well as high methyl-transalkylation activity to improve the yield of xylenes. High ethyl-dealkylation activity is considered total MEB conversion above 70% at 350° C. Dealkylation of MEB is not limited by thermodynamic equilibrium, so total MEB conversion of 100% is the target. Additionally, high methyl-transalkylation activity is considered conversions of TMB above 40% at 350° C. Transalkylation is a reaction limited by thermodynamic equilibrium, so TMB conversion cannot surpass values in the range of 51-52% at temperatures ranging from 300-450° C., thus total TMB conversion of 51% is the target.

According to one embodiment, a method of forming a composite zeolite catalyst is provided. The method includes combining a silicon source and an aqueous organic structure directing agent to form a silica intermediary gel. The aqueous organic directing structure agent includes a polyamino cation compound. The method also includes introducing an aluminum precursor to the silica intermediary gel to form a catalyst precursor gel and evaporating the water in the catalyst precursor gel to form a catalyst gel. Finally, the method includes heating the catalyst gel to form a composite zeolite catalyst particle with both Beta and ZSM-5 zeolites characterized by having an intergrowth region with a mixture of both Beta crystals and ZSM-5 crystals.

According to another embodiment, a composite zeolite catalyst is provided. The composite zeolite catalyst comprises ZSM-5 and Beta within a single catalyst particle. Further, the composite zeolite catalyst has an intergrowth region with a mixture of beta crystals and ZSM-5 crystals, the intergrowth of ZSM-5 and Beta characterized by an XRD pattern having signature peaks at 7.6±0.2, 7.9±0.2, 8.8±0.2, 22.4±0.2, 23.1±0.2 and 23.9±0.2.

According to yet another embodiment, a method of making xylene is provided. The method includes feeding heavy reformate to a reactor. The reactor contains a composite zeolite catalyst including a plurality of catalyst particles. Each catalyst particle includes both ZSM-5 and Beta zeolites and has an intergrowth region with a mixture of both Beta crystals and ZSM-5 crystals. Further the method includes producing xylene by performing transalkylation and dealkylation of the heavy reformate in the reactor, where each catalyst particle is able to simultaneously catalyze both the transalkylation and dealkylation reactions.

According to another embodiment, a system for making xylene is provided. The system includes a reactor. The reactor contains a composite zeolite catalyst including a plurality of catalyst particles. Each catalyst particle includes both ZSM-5 and Beta zeolites and has an intergrowth region with a mixture of both Beta crystals and ZSM-5 crystals.

Additional features and advantages of the described embodiments will be set forth in the detailed description which follows, and in part will be readily apparent to those skilled in the art from that description or recognized by practicing the described embodiments, including the detailed description which follows, the claims, as well as the appended drawings.

DETAILED DESCRIPTION

Reference will now be made in detail to embodiments of a method of forming a composite zeolite catalyst and conversion of heavy reformate with the composite zeolite catalyst.

The main components of heavy reformate are ethyltoluenes (methyl-ethyl-benzenes, MEB) and trimethyl-benzenes (TMB). The structures of the MEB isomers and TMB isomers are provided infra.

MEB isomers

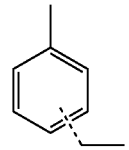

(para, meta and ortho)

TMB isomers

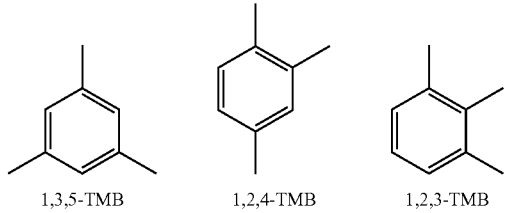

1,3,5-TMB     1,2,4-TMB     1,2,3-TMB

These aromatics can be converted into the more valuable BTEX compounds by means of dealkylation of the $C_{9+}$ alkylaromatics, or by transalkylation of these compounds with benzene or toluene. The aim of the process is to maximize the production of xylenes by de-ethylation of MEB and transalkylation of TMB. Specifically, transalkylation of TMB present in the feed with the toluene formed as a product of de-ethylation of MEB.

The dealkylation of MEB to toluene and ethane is provided infra. Dealkylation of MEB in the presence of a Brønsted acid catalyst initially produces toluene and ethylene. However, the ethylene may be subsequently hydrogenated to ethane in the presence of an adequate hydrogenation catalyst. If the hydrogenation functionality is not effective, portions of the ethylene may not be hydrogenated to ethane and as such may be present in the product gases, or it may be converted to oligomers or other products.

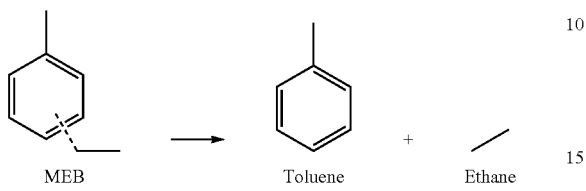

The transalkylation of TMB present in the heavy reformate with the toluene formed from dealkylation of MEB to toluene and ethane is provided infra.

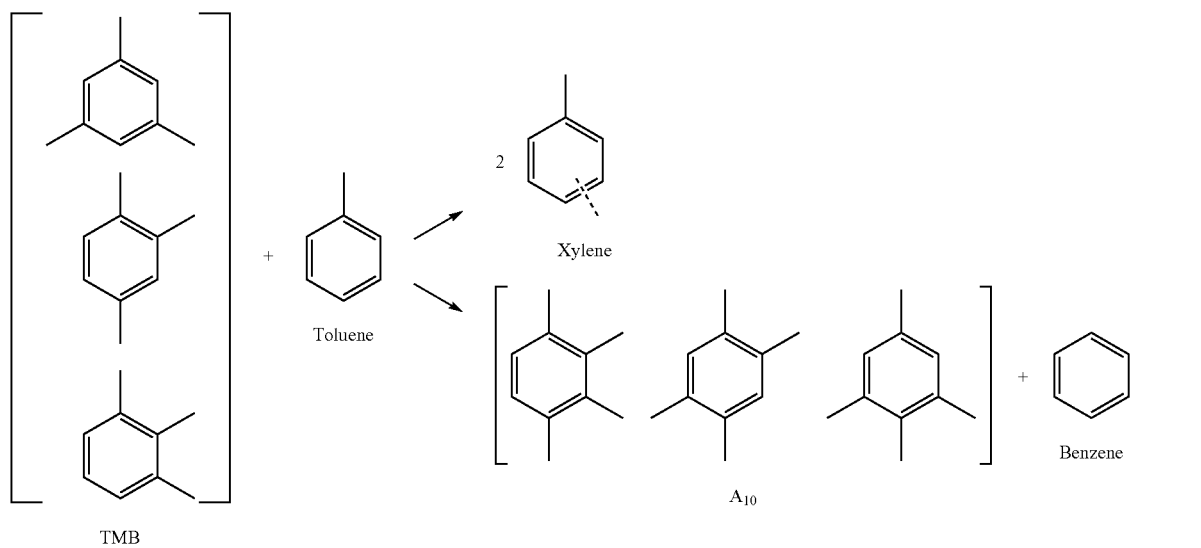

Additionally, toluene and TMB may also undergo a disproportionation reaction leading to xylenes and benzene or xylenes and tetramethylbenzenes ($A_{10}$), respectively. The chemical reactions are provided infra.

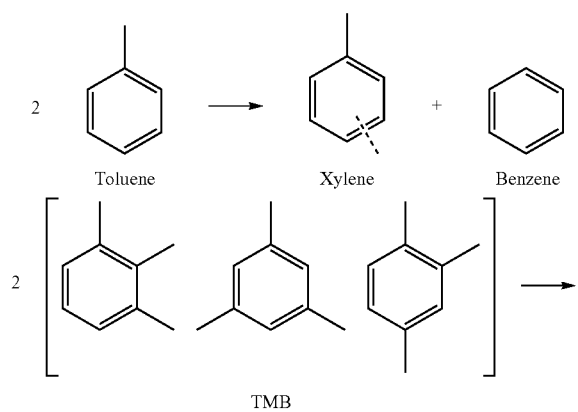

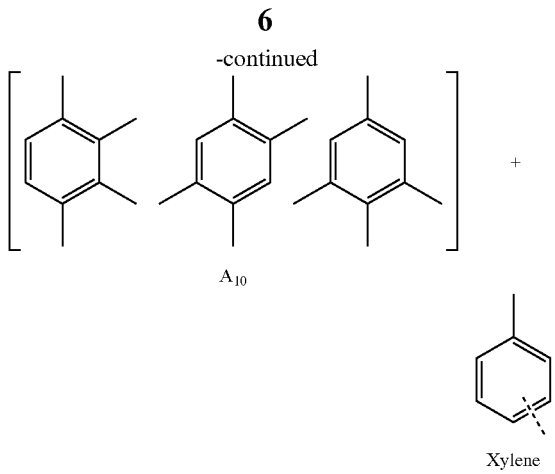

The method of forming a composite zeolite catalyst includes combining a silicon source and an aqueous organic structure directing agent in a reagent container to form a silica intermediary gel. Subsequently, alumina is added to the silica intermediary gel to form a catalyst precursor gel. The catalyst precursor gel is continuously stirred for homogenization while evaporating the water in the catalyst precursor gel. Stirring is continued until a desired amount of water remains in the catalyst precursor gel to form a catalyst gel. The catalyst gel is then heated in a sealed vessel under autogenous pressure to form the composite zeolite catalyst. The formed composite zeolite catalyst is a bulk catalyst without an underlying support matrix.

The composite zeolite catalyst in one or more embodiments comprises Beta and ZSM-5. ZSM-5 is a aluminosilicate zeolite of the pentasil family of zeolites. ZSM-5 (Zeolite Socony Mobil-5) has a Mordenite Framework Inverted (MFI) framework with an ordered crystal structure. Zeolite Beta, an aluminosilicate with a BEA framework, is defined by an intergrowth of two distinct polymorphs which are arranged randomly within the structure.

Figure 3A:
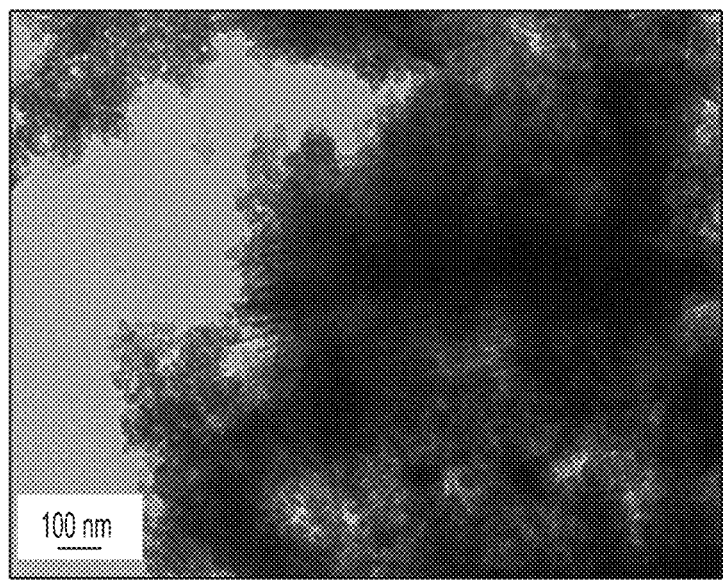
FIG. 3A is a TEM micrograph of a composite zeolite catalyst with a Beta to ZSM-5 ratio of 60:40 synthesized in accordance with one or more embodiments of the present disclosure.
Figure 3B:
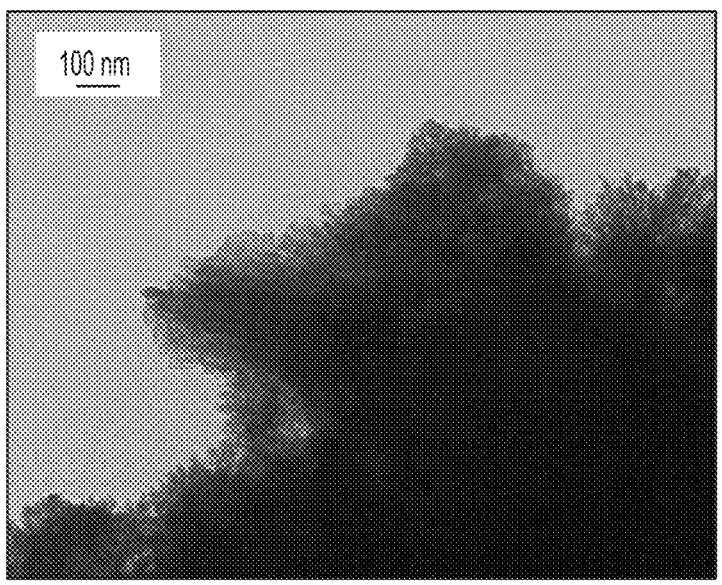
FIG. 3B is a TEM micrograph of a composite zeolite catalyst with a Beta to ZSM-5 ratio of 40:60 synthesized in accordance with one or more embodiments of the present disclosure.

The simultaneous crystallization of both ZSM-5 and Beta from the catalyst gel generates a final particle of composite zeolite catalyst with both Beta and ZSM-5 in intimate contact at the nanometer scale. As used in this disclosure, "intimate contact" means the Beta and ZSM-5 are intermixed within a single particle of the composite zeolite catalysts such that crystals of ZSM-5 and crystals of Beta are abutting when viewed at a nanoscale level. The ZSM-5 and Beta crystals are dispersed throughout the composite zeolite catalyst and form an intimate mixture of both ZSM-5 and Beta crystals interwoven within the same particle of the composite zeolite catalyst, as can be concluded from the TEM images shown in FIG. 3. The area of interwoven ZSM-5 and Beta crystals is termed the intergrowth region. The intergrowth region includes distinct crystals of ZSM-5 and Beta, but their simultaneous formation results in the crystals of each type in intimate contact at the nanometer scale. The intimate mixing of the ZSM-5 and Beta crystals enhances the consecutive dealkylation-transalkylation reactions desired for conversion of the industrial heavy reformate into xylenes by reducing the transport distance of reaction products between zeolite types. In this way, the composite zeolite catalyst allows one-pot dealkylation of the MEB in heavy reformate and transalkylation of the TMB The aqueous organic structure directing agent may comprise water and one or more polyamino cations. In embodiments, the aqueous organic structure directing agent comprises between 5 and 15 wt. % polyamino cations and between 85 and 95 wt. % water. In various further embodiments, the aqueous organic structure directing agent comprises between 8 and 13 wt. % polyamino cations and between 87 and 92 wt. % water, or the aqueous organic structure directing agent comprises between 9 and 12 wt. % polyamino cations and between 88 and 91 wt. % water. In embodiments, the polyamino cations may comprise a $N_4$-phe-$C_n(OH)_4$ structure, with "n" varying in the range of 6 to 22. In one specific embodiment, the polyamino cations may comprise the $N_4$-phe-$C_6(OH)_4$ structure provided infra. The organic structure directing agent directs the synthesis process towards crystallization of the desired species. For this disclosure the organic structure directing agent directs the synthesis towards crystallization of nanocrystals of ZSM-5, Beta structure, or both, depending on the composition of the synthesis gel.

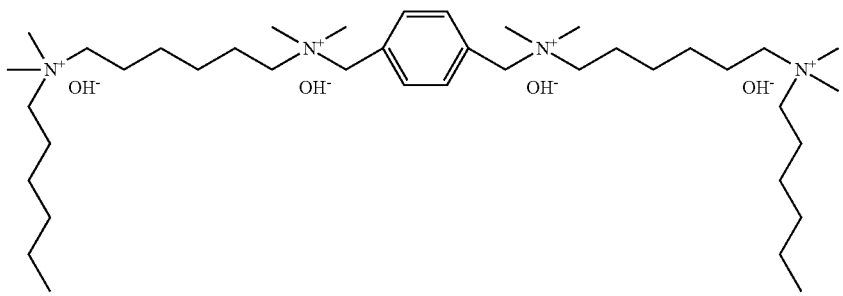

with the in-situ produced toluene to achieve maximum xylenes selectivity and catalyst performance.

When used as a catalyst for conversion of heavy reformate, the composite zeolite catalyst achieves improved performance as compared to monozeolitic based catalysts or as compared to multizeolitic based catalyst prepared by physical mixtures of the individual zeolite components. This improvement is even more profound when carrying out the transalkylation of a heavy reformate in the absence of added toluene or benzene, because these two aromatics must be produced in-situ from $C_{9+}$ aromatics such as with dealkylation of MEB contained within the feed. The intimate contact of the Beta and ZSM-5 in the composite zeolite catalyst produced in accordance with this disclosure allows the toluene produced from dealkylation of MEB to be more readily available for use in the transalkylation reaction of TMB or disproportionation reaction of toluene for the ultimate production of xylenes.

In one or more embodiments, the silicon source is a silica gel. The silica gel may be a 20 to 60 weight percent (wt. %) suspension of silica in water, a 25 to 55 wt. % suspension of silica in water, a 30 to 50 wt. % suspension of silica in water, or a 35 to 45 wt. % suspension of silica in water. The silicon source may also be silicon oxide, silicon halide, tetraalkyl orthosilicate, silicate, silicic acid, fumed silica, sodium silicate, colloidal silica, a previously synthesized crystalline material, a previously synthesized amorphous material and combinations thereof. For example, the silicon source may be Ludox AS-40 (W.R. Grace & Co.—Conn.), which is a 40 wt. % suspension of colloidal silica in water. According to manufacturer specifications, the particle size of Ludox AS-40 is 20-24 nm.

The silicon source is combined with the aqueous organic structure directing agent and stirred vigorously to form the silica intermediary gel. The aqueous organic structure directing agent has a high pH in the range of 9 to 14. The higher the concentration of the organic structure directing agent in the silica intermediary gel the higher the final pH will be of the silica intermediary gel. Under the elevated pH basic conditions, the silicon source, such as Ludox AS-40, is dissolved and mobilized.

The catalyst precursor gel is formed by adding an aluminum precursor to the silica intermediary gel. From the dissolved silicon source new species form, which react with each other and with the aluminum species in solution to form the crystalline zeolite structure. In one or more embodiments, the aluminum precursor is an alumina ($Al_2O_3$), aluminum hydroxide ($Al(OH)_3$), aluminum oxide hydroxide (AlO(OH)) (also called boehmite), or combinations thereof. Other compositions are also contemplated for the aluminum precursor. A suitable commercial embodiment of the aluminum precursor may be CATAPAL A, a boehmite from Sasol. For clarity, CATAPAL A is a hydrated alumina, that can be expressed as AlO(OH) or as 74.6 wt. % of $Al_2O_3$ in $H_2O$. In various embodiments, the aluminum precursor has a concentration of 60 to 100% by weight, 65 to 90% by weight, 70 to 80% by weight or 72 to 78% by weight of $Al_2O_3$ in $H_2O$. The silica intermediary gel and the alumina are stirred continuously to ensure homogenization of the formed catalyst precursor gel. If homogenization is not achieved crystallization of other silica or alumina phases may compete with the desired ZSM-5 and Beta. Stirring is continued until the final catalyst precursor gel composition, and more specifically the desired water level, is obtained. As the catalyst precursor gel is stirred the water within the gel evaporates reducing the water content to the desired level. The catalyst precursor gel initially includes an excess of water. Therefore, the catalyst gel is stirred and the water evaporated until the water content matches the one given in the gel compositions provided infra in Table 1.

The catalyst precursor gel after water evaporation is termed the catalyst gel. The composition of the catalyst gel varies depending on the desired ZSM-5 and Beta ratio of the final composite zeolite catalyst. Formation of pure Beta utilizes a catalyst gel composition of 1 $SiO_2$:0.025 $Al_2O_3$: 0.125 polyamino cation:20$H_2O$ on a molar basis. Formation of pure ZSM-5 utilizes a catalyst gel composition of 1 $SiO_2$:0.01 $Al_2O_3$:0.01 polyamino cation:20$H_2O$. Formation of 40 wt. % Beta and 60 wt. % ZSM-5 utilizes a catalyst gel composition of 1 $SiO_2$:0.0167 $Al_2O_3$:0.075 polyamino cation:20$H_2O$. Formation of 60 wt. % Beta and 40 wt. % ZSM-5 utilizes a catalyst gel composition of 1 $SiO_2$:0.025 $Al_2O_3$:0.075 polyamino cation:20$H_2O$. It will be appreciated that other ratios such as 80 wt. % Beta and 20 wt. % ZSM-5 or 20 wt. % Beta and 80 wt. % ZSM-5 may be achieved by adjusting the ratios of aluminum precursor and aqueous organic structure directing agent in the catalyst precursor gel and the ultimate catalyst gel accordingly. Determination of sufficient water removal may be made based on when the weight of the catalyst precursor gel matches the expect weight of the target composition delineated supra. As water is the only volatile component of the catalyst precursor gel, the remaining components will remain in solution allowing the weight of the catalyst precursor gel to serve as a direct measurement of the amount of water removed.

Subsequently, in one or more embodiments, the catalyst gel is heated in a sealed vessel under autogenous pressure in combination with stirring. Autogenous pressure is the pressure naturally produced by heating within a closed and sealed vessel. In one or more embodiments, the catalyst gel is introduced into an oven heated to between 130 and 180° C. In addition to placement in a heated oven, other heating methods such as introduction to a heated autoclave or coverage with a heating jacket are also contemplated as suitable. In various further embodiments, the catalyst gel is introduced into the sealed vessel heated to between 135 and 170° C., 140 and 160° C., or approximately 150° C. Additionally, in various embodiments, the heating of the catalyst gel in the sealed vessel is maintained with stirring for 4 to 15 days, 5 to 10 days, 6 to 8 days, or approximately 7 days. Additionally, stirring of the catalyst gel during heating in the sealed vessel under autogenous pressure may be maintained at approximately 10 to 100 rotations per minute (rpm), 20 to 90 rpm, 30 to 80 rpm, 40 to 75 rpm, 50 to 70 rpm, or 55 to 65 rpm for the entirety or only a portion of the heating cycle. It is envisioned that stirring speed may vary over the course of the heating cycle, such as with a speed of approximately 60 rpm for a first period and approximately 20 rpm for a second period.

In at least one embodiment, the catalyst gel is heated in a vessel allowing for a continuous process. In one or more embodiments, the catalyst gel is introduced into an oven, such as a tunnel oven, heated to between 130 and 180° C. In various further embodiments, the catalyst gel is introduced into the vessel heated to between 135 and 170° C., 140 and 160° C., or approximately 150° C.

The composite zeolite catalyst may further be calcined. In one or more embodiments the composite zeolite catalyst is calcined at a temperature of 550° C. for 5 hours in air, after increasing temperature in a $N_2$ flow at a rate of 3° C. per minute (min).

The specific catalyst gel compositions and the use of the organic structure directing agent are able to direct the synthesis process to the simultaneous crystallization of both Beta and ZSM-5. The organic structure directing agent allows for the crystallization of the ZSM-5 and Beta as single phases or as intimate mixtures, with crystals in the nanometer range. The catalyst gel composition determines the proportion of ZSM-5 and Beta in the final solid.

Figure 1A:
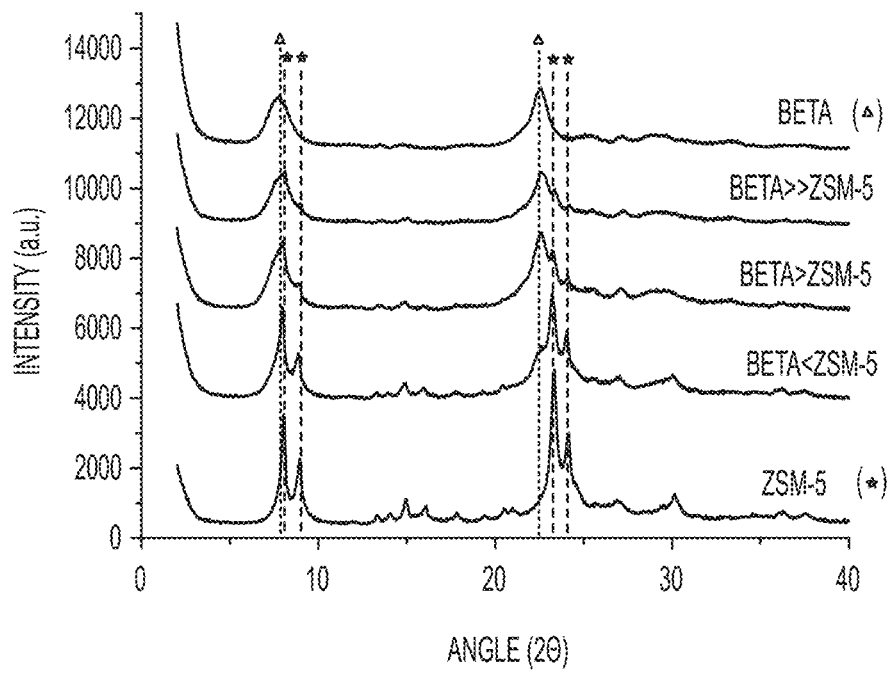
FIG. 1A is an X-Ray Diffraction (XRD) pattern of composite zeolite catalysts synthesized in accordance with one or more embodiments of the present disclosure.
Figure 1B:
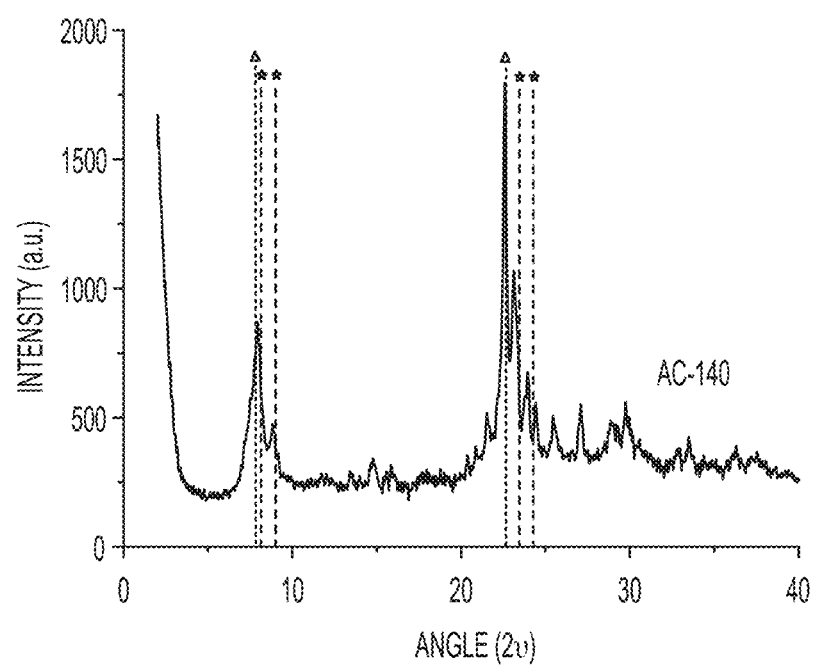
FIG. 1B is an X-Ray Diffraction (XRD) pattern of comparative catalyst AC-140.

The ratio of ZSM-5 and Beta within the composite zeolite catalyst may be determined with X-ray diffraction (XRD) analysis. The X-ray diffraction patterns for pure phase Beta and ZSM-5 are distinct with representative peaks. Identification of the distinct peaks representing ZSM-5 and Beta respectively in an X-ray diffraction pattern for a catalyst sample with each zeolite type present allows a determination of the proportion of each zeolite in the mixture. Example XRD patterns for pure phase Beta, pure phase ZSM-5, as well as differing ratios of Beta and ZSM-5 are provided in FIG. 1. Two distinct peaks are observed for Beta at 7.6 and 22.4 (2θ degree), marked with triangles, and four distinct peaks in groupings of two are observable for ZSM-5 at 7.9, 8.8, 23.1 and 23.9 (2θ degree), marked with stars. The XRD patterns for 80:20 Beta:ZSM-5, 60:40 Beta:ZSM-5, and 40:60 Beta:ZSM-5 include varying relative intensity of each of the six distinct peaks as the ratio of Beta to ZSM-5 varies.

Figure 2A:
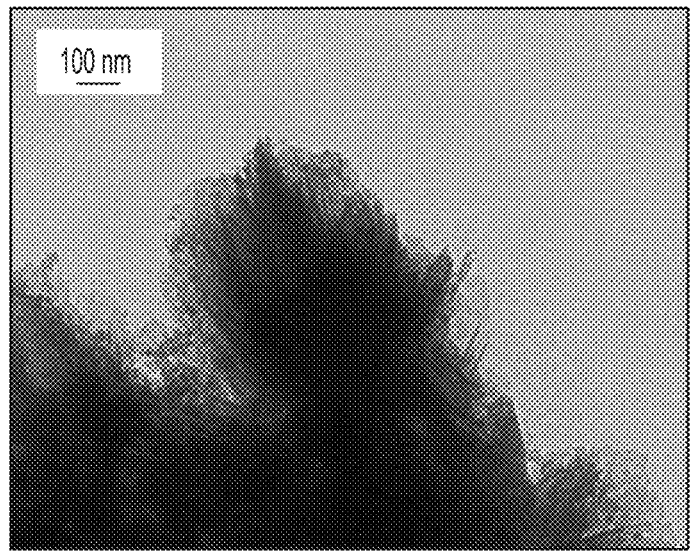
FIG. 2A is a Transmission Electron Microscopy (TEM) micrograph of pure ZSM-5 synthesized in accordance with one or more embodiments of the present disclosure.
Figure 2B:
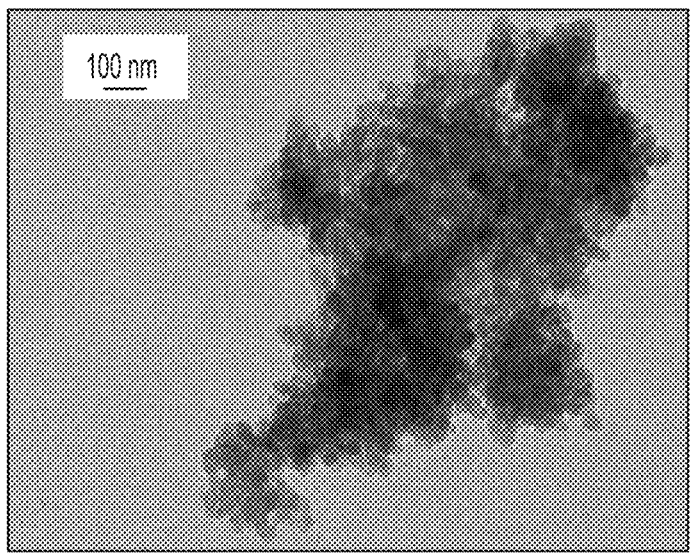
FIG. 2B is a TEM micrograph of pure Beta synthesized in accordance with one or more embodiments of the present disclosure.

The Beta and ZSM-5 components of the composite zeolite catalyst are formed in intimate contact at the nanocrystal level. For purposes of this disclosure, crystals with sizes below 0.1 microns are considered nanocrystals. The ZSM-5 and Beta are present as individual crystals with their own respective unique morphology. The ZSM-5 crystallizes as layers, whereas Beta crystallizes as nanocrystals. With reference to FIGS. 2A and 2B and FIGS. 3A and 3B, transmission electron microscopy (TEM) micrographs are provided of pure ZSM-5, pure Beta, and composite ZSM-5/Beta zeolite catalysts formed in accordance with the present disclosure. FIG. 2A illustrates the layered crystalline formations of the pure ZSM-5 and FIG. 2B illustrates the nanocrystalline nature of the pure Beta. Additionally, the combination of nanocrystal and layer formation is visible in the composite zeolite catalysts samples illustrated in FIGS. 3A and 3B. The presence of a majority of nanocrystal (Beta) is visible in FIG. 3A for a composite zeolite catalyst with a 60:40 weight ratio of Beta:ZSM-5. Similarly, the presence of a majority of layered crystal (ZSM-5) is visible in FIG. 3B for a composite zeolite catalyst with a 40:60 weight ratio of Beta:ZSM-5.

Moreover, the zeolite composite catalysts may be impregnated with metals for catalysis, for example, metals such as molybdenum, chromium, platinum, nickel, tungsten, palladium, ruthenium, gold, rhenium, rhodium, or combinations thereof. In one embodiment, the impregnated metal is rhenium (Re). The metal component may exist within the final catalytic composite as a compound, such as an active metal oxide, an active metal sulfide or active metal halide, in chemical combination with one or more of the other ingredients of the composite, or as an elemental metal. The impregnated metal component may be present in the final zeolite composite catalyst in any amount that is catalytically effective, for example from 0.01 to 20.0 wt. %, or from 0.05 to 5 wt. %, or from 0.1 to 1.5 wt. %, or approximately 0.5 wt. % of the zeolite catalyst.

Metals are added to the catalyst for their hydrogenation functionality. The dealkylation, transalkylation and disproportionation reactions take place on the Brønsted acid sites of the composite zeolite catalysts. However, the hydrogenation function of the metal component is utilized to convert ethylene into ethane and may also enhance the desorption of coke precursors. The conversion of ethylene into ethane avoids the oligomerization of the olefin to products that may deactivate the catalyst.

In one or more embodiments, the metals are incorporated to the catalyst by ion exchange or impregnation of their salts in aqueous solution. The catalysts with the incorporated metals are then calcined in air and the metals are converted into their oxide forms, which do not present hydrogenation activity. In order to be active for hydrogenation these oxides are converted into metal sulfides, for example metal sulfides of Mo, Ni, or W, or the metal oxides can be reduced to their elemental metal form, for example elemental forms of Mo, Pt, Re, Pd, or Rh. In one or more embodiments, the composite zeolite catalyst is impregnated with rhenium in the form of ammonium perrhenate ($NH_4ReO_4$) through an incipient wetness procedure. In one or more embodiments, the composite zeolite catalyst is impregnated with molybdenum in the form of ammonium molybdate tetrahydrate (($NH_4)_6Mo_7O_{24} \cdot 4H_2O$) through an incipient wetness procedure.

In one embodiment, the molar ratio of silicon to aluminum (Si/Al) in the zeolite composite catalyst is from 15 to 55. In further embodiments, the molar ratio of silicon to aluminum in the zeolite composite catalyst is from 17 to 42 or from 18 to 26. It will be appreciated that the molar ratio of silicon to aluminum varies depending on the ratio of Beta and ZSM-5 in the composite zeolite catalyst. It is noted, the final Si/Al molar ratio in the zeolite composite catalyst depends on the degree of incorporation of the silicon and aluminum species into the final crystalline zeolite. Due to the basicity of the synthesis media, a small fraction of the starting silicon may remain in solution and may not be incorporated in the zeolitic framework thereby decreasing the final Si/Al ratio of the zeolite composite catalyst as compared to the starting Si/Al ratio in the catalyst gel.

From a property standpoint, in one or more embodiments, the composite zeolite catalyst may have a micropore volume ($V_{micro}$) of at least 0.10 cubic centimeters per gram ($cm^3/g$), or a micropore volume of at least 0.15 $cm^3/g$, or a micropore volume of 0.10 to 0.20 $cm^3/g$. The micropore volume may be calculated by the t-plot method of determining micropore volume known to one having skill in the art. Similarly, in one or more embodiments, the composite zeolite catalyst may have a mesopore volume ($V_{meso}$) of at least 0.30 cubic centimeters per gram ($cm^3/g$), or a mesopore volume of at least 0.33 $cm^3/g$, or a mesopore volume of 0.3 to 0.45 $cm^3/g$. The mesopore volume may be calculated according to the Barrett-Joiner-Halenda (BJH) method of determining mesopore volume known to one having skill in the art. Details regarding the t-plot method and the BJH method of calculating micropore volume and mesopore volume respectively are provided in Galarneau et al., "Validity of the t-plot Method to Assess Microporosity in Hierarchical Micro/Mesoporous Materials", Langmuir 2014, 30, 13266-13274, for example.

The micropore volume and the mesopore volume represent the specific volumes corresponding to the microporous structure and to the mesoporous structure, respectively. The mesopores are mainly due to intercrystalline voids formed because of the very small size of the zeolite crystals. The pore size ranges for mesopores and micropores are in conformity with conventionally understood size ranges for such pore classifications with micropores representing pores under 2 nanometers (nm) in diameter and mesopores representing pores of 2 to 50 nm in diameter. A total pore volume would additionally include any macropores if present.

In one or more embodiments, the composite zeolite catalyst may have a surface area defined by a Brunauer-Emmett-Teller (BET) analysis ($S_{BET}$) of at least 450 square meters per gram ($m^2/g$), or a $S_{BET}$ surface area of at least 500 $m^2/g$. Further, the composite zeolite catalyst may have a micropore surface area ($S_{micro}$) of 300 $m^2/g$ to 360 $m^2/g$. The micropore surface area may be calculated directly from the micropore volume. Additionally, the zeolite composite catalyst may have an external surface area ($S_{Ext}$) of at least 100 $m^2/g$, and preferentially, it may have an external surface area of 150 $m^2/g$ to 360 $m^2/g$. It is noted that the external surface area is obtained as the difference between the BET surface area and the micropore surface area.

The composite zeolite catalyst allows conversion of heavy reformate, or other aromatic reactant streams, in a single reactor. Specifically, the dealkylation of MEB and the transalkylation of the produced toluene with TMB may be performed in a single reactor because of the intimate contact between the crystals of Beta and ZSM-5. The MEB dealkylation reaction is necessary in order to obtain the toluene that has to react with the TMB in the feed for producing the desired xylenes. Thus, the intimate proximity of the ZSM-5 and Beta crystals obtained by the one pot synthesis of the composite zeolite catalyst enables an improved and faster coupling of both consecutive reactions as compared with conventional multizeolite catalysts.

Alkylaromatics, such as those present in a heavy reformate (MEB, TMB), in the presence of an acid catalyst, may undergo undesired reactions which lead to formation of aromatics with more than 10 carbon atoms ($A_{10+}$). If these $A_{10+}$ compounds cannot diffuse out of the zeolite crystals through the pores of the crystalline structure because of steric limitations, they may block part of the channel systems or lead to bulkier coke precursors. The improved conversion efficiency of the composite zeolite catalysts alleviates the formation of heavy alkylaromatics. Specifically, the proximity of the ZSM-5 and Beta allows the TMB of the feed to react preferentially with the toluene formed by dealkylation of MEB on the ZSM-5 crystals, instead of reacting with other TMB by transalkylation to form tetramethylbenzene or heavier compounds. Additionally, the small crystal size of ZSM-5 and Beta, and therefore short diffusion pathways, allow any primary products to diffuse out of the zeolite crystals before being able to react and form heavier aromatics, coke precursors, or both. The specific properties of the composite zeolite catalyst, including small crystal size and intimate proximity of the ZSM-5 and Beta at the nanometer scale, results in higher selectivity to xylenes and reduced formation of $A_{10+}$ and coke precursors, leading therefore to improved catalyst life.

Examples

The described embodiments will be further clarified by the following examples and comparative examples.

For demonstration purposes, composite zeolite catalysts were prepared in accordance with one or more embodiments of this disclosure. The composite zeolite catalysts were formed with varying ratios of Beta and ZSM-5. Pure Beta was synthesized and designated Beta. Pure ZSM-5 was synthesized and designated ZSM-5. Composite zeolite catalyst was synthesized with a weight ratio of 40% Beta and 60% ZSM-5 and designated Beta<ZSM-5. Composite zeolite catalyst was synthesized with a weight ratio of 60% Beta and 40% ZSM-5 and designated Beta>ZSM-5. Composite zeolite catalyst was synthesized with a weight ratio of 80% Beta and 20% ZSM-5 and designated Beta>>ZSM-5. To synthesize the composite zeolite catalyst Beta>ZSM-5, 22.5 g of the silicon source (Ludox AS-40, Sigma-Aldrich) was added to 71.58 g of a solution of $N_4$-phe-$C_6(OH)_4$ (10.8 wt % of $N_4$-phe-$C_6(OH)_4$ in $H_2O$) and stirred vigorously. To this mixture, 0.51 g of the aluminum source (CATAPAL A, 74.6%, SASOL) was added and the resulting gel was stirred continuously until reaching the desired amount of water in the gel. The desired amount of water in the gel was determined to have been reached when the mass of the gel matched the expected mass based on Table 1 provide infra for the desired Beta:ZSM-5 ratio. In a final step, the gel with the desired composition was introduced into a 35 ml Teflon-lines autoclave at 150° C. under stirring at 60 rpm and autogenous pressure for 7 days. The synthesis gels for the rest of the composite zeolite catalysts, pure Beta, pure ZSM-5, Beta<ZMS-5 and Beta>>ZMS-5 are prepared in a similar way with the ratio of components adjusted to match the molar ratios provided in Table 1.

TABLE 1

Gel Compositions

| Sample | Composition |
| --- | --- |
| Beta (Si/Al = 20) | 1 $SiO_2$:0.025 $Al_2O_3$:0.125 $N_4$-phe-$C_6(OH)_4$:20 $H_2O$ |
| ZSM-5 (Si/Al = 50) | 1 $SiO_2$:0.01 $Al_2O_3$:0.01 $N_4$-phe-$C_6(OH)_4$:20 $H_2O$ |
| Beta < ZSM-5 (Si/Al = 30) | 1 $SiO_2$:0.0167 $Al_2O_3$:0.075 $N_4$-phe-$C_6(OH)_4$:20 $H_2O$ |
| Beta > ZSM-5 (Si/Al = 20) | 1 $SiO_2$:0.025 $Al_2O_3$:0.075 $N_4$-phe-$C_6(OH)_4$:20 $H_2O$ |
| Beta >> ZSM-5 (Si/Al = 20) | 1 $SiO_2$:0.025 $Al_2O_3$:0.1 $N_4$-phe-$C_6(OH)_4$:20 $H_2O$ |

Composite zeolite catalysts were also synthesized with rhenium incorporated into the catalyst. Rhenium was incorporated into each sample pure Beta, pure ZSM-5, Beta<ZSM-5, Beta>ZSM-5, and Beta>>ZSM-5 to generate samples designated as Re/Beta, Re/ZSM-5, Re/Beta<ZSM-5, Re/Beta>ZSM-5, and Re/Beta>>ZSM-5 respectively. Rhenium was incorporated into all of the samples at 0.5 wt. % by means of the incipient wetness procedure using ammonium perrhenate ($NH_4ReO_4$) as a metal precursor.

The physico-chemical properties of each of the samples were quantified. Specifically, the silicon to aluminum ratio as well as the final wt. % of Re in each sample was determined for each sample type. Additionally, the micropore volume and the mesopore volume were calculated according to the t-plot method and the BJH correlation method respectively. Further, the micropore surface area was calculated from the micropore volume, the total specific surface area was calculated in accordance with the Brunauer-Emmett-Teller method widely used for evaluating the surface area of porous and finely-divided materials, and the external surface area was calculated based on the difference between the total specific surface area and the micropore surface area. These physio-chemical properties are delineated in Table 2 provide infra.

TABLE 2

Chemical composition and textural properties of samples

| Sample | Si/Al | Re (wt. %) | $S_{BET}$ (m²/g) | $S_{micro}$ (m²/g) | $S_{Ext}$ (m²/g) | $V_{micro}$ (cm³/g) | $V_{meso}$ (cm³/g) |
| --- | --- | --- | --- | --- | --- | --- | --- |
| Beta | 17.5 | — | 633 | 337 | 296 | 0.16 | 0.41 |
| Re/Beta | 17.5 | 0.47 | 614 | 315 | 298 | 0.15 | 0.42 |
| Beta >> ZSM-5 | 18.1 | — | 687 | 332 | 355 | 0.16 | 0.42 |
| Re/Beta>>ZSM-5 | 16.7 | 0.41 | 628 | 306 | 322 | 0.15 | 0.38 |
| Beta > ZSM-5 | 17.6 | — | 642 | 349 | 293 | 0.17 | 0.39 |
| Re/Beta > ZSM-5 | 16.7 | 0.52 | 595 | 316 | 278 | 0.15 | 0.39 |
| Beta < ZSM-5 | 25.8 | — | 569 | 356 | 212 | 0.17 | 0.34 |
| Re/Beta < ZSM-5 | 25.5 | 0.45 | 550 | 343 | 207 | 0.17 | 0.34 |
| ZSM-5 | 37.4 | — | 513 | 346 | 167 | 0.17 | 0.34 |
| Re/ZSM-5 | 40.5 | 0.53 | 505 | 336 | 170 | 0.16 | 0.37 |

Table 2 illustrates that the Beta and ZSM-5 composite zeolite catalysts have properties which correlate with the proportion of Beta and ZSM-5 in the final composite zeolite catalyst. The Si/Al ratio, $S_{BET}$, $S_{micro}$, $S_{ext}$, $V_{micro}$, and $V_{meso}$ each follow a generally increasing or decreasing pattern from the value for pure Beta to the value for pure ZSM-5 as the ratio of ZSM-5 increases. For example, as the proportion of ZSM-5 increases in the composite zeolite catalyst sample, the $S_{BET}$ decreases and approaches the value presented for pure ZSM-5. Additionally, the $V_{meso}$ values suggest that the crystal size of these zeolites is very small because the mesopore volume is high which indicates intercrystalline void spaces. This analysis is confirmed by the TEM micrographs of FIGS. 2A, 2B, 3A, and 3C which visually illustrate the small crystal size of the zeolites.

The acidic properties of each of the samples were also quantified. Acidity measurements were carried out by adsorption/desorption of pyridine followed by IR spectroscopy. Self-supported wafers (10 mg $cm^{-2}$) of calcined samples, previously activated at 400° C. and $10^{-2}$ Pa overnight in a Pyrex vacuum cell, were allowed to come in contact with $6.5 \times 10^2$ Pa of pyridine vapor at room temperature and desorbed in vacuum at increasing temperatures (150, 250, and 350° C.). The spectra were recorded at room temperature. All the spectra were scaled according to the sample weight. Brønsted and Lewis acidity of the samples compared are given in arbitrary units, according to the intensity of the bands assigned to the pyridine interacting with the Brønsted and Lewis acid sites of the zeolites (1550 and 1450 $cm^{-1}$, respectively). These acidic properties are listed in Table 3 provide infra.

TABLE 3

Acidic properties of samples

| Sample | Brønsted Acidity (u.a.) | | | | Lewis Acidity (u.a.) | | |
| --- | --- | --- | --- | --- | --- | --- | --- |
|  | B150 | B250 | B350 | B350/B150 | L150 | L250 | L350 |
| Beta | 116 | 104 | 70 | 0.60 | 223 | 216 | 185 |
| Re/Beta | 139 | 114 | 62 | 0.45 | 209 | 186 | 154 |
| Beta >> ZSM-5 | 166 | 136 | 108 | 0.65 | 221 | 201 | 175 |
| Re/Beta>>ZSM-5 | 139 | — | — | — | 160 | — | — |
| Beta > ZSM-5 | 129 | 112 | 77 | 0.60 | 213 | 193 | 170 |
| Re/Beta > ZSM-5 | 167 | 125 | 95 | 0.57 | 260 | 225 | 147 |
| Beta < ZSM-5 | 110 | 118 | 82 | 0.75 | 148 | 146 | 131 |
| Re/Beta < ZSM-5 | 124 | 97 | 69 | 0.56 | 158 | 127 | 94 |
| ZSM-5 | 62 | 51 | 61 | 0.98 | 58 | 43 | 67 |
| Re/ZSM-5 | 114 | 95 | 73 | 0.64 | 113 | 103 | 83 |
| AC-140 | 125 | 90 | 56 | 0.45 | 315 | 259 | 185 |

Table 3 illustrates that the composite zeolite catalyst samples where Beta is in larger proportion than ZSM-5

(Beta>>ZSM-5 and Beta>ZSM-5 samples) present a higher Brønsted acidity as compared to the pure Beta and pure ZSM-5 zeolites obtained by means of the same synthesis procedure. Thus, regarding the acidic properties, it can be concluded that synthesis of Beta and ZSM-5 mixtures as a composite zeolite catalyst in a single vessel with simultaneous crystallization and intimate contact of the ZSM-5 and Beta, as with the present disclosure, is an improvement upon previous attempts at merely physically mixing Beta and ZSM-5 together.

As stated supra, the present composite zeolite catalyst is a dealkylation and transalkylation catalyst suitable for converting $C_{9+}$ alkyl aromatic hydrocarbons to a product stream comprising benzene, toluene, and xylenes, particularly to commercially valuable xylenes. The feed stream to the conversion process generally comprises alkylaromatic hydrocarbons in the carbon number range $C_9$ to $C_{11+}$ that may include, for example, such hydrocarbons as propylbenzenes, methylethylbenzenes, tetramethylbenzenes, ethyldimethylbenzenes, diethylbenzenes, methylpropylbenzenes, and mixtures thereof. For purposes of testing and quantifying the examples and comparative examples a simulated heavy reformate feed was generated. The simulated heavy reformate feed comprised 30 wt. % para-methylethylbenzene (p-MEB) and 70 wt. % 1,2,4-trimethylbenzene (1,2,4-TMB).

Catalytic tests for conversion of the simulated heavy reformate feed were performed in a reaction system comprising 16 continuous fixed-bed parallel microreactors. Each reactor was capable of being fed independently with the desired flow of the simulated reformate feed and $H_2$ making it possible to operate in a wide range of contact times and hydrogen/hydrocarbon molar ratios. The simultaneous catalytic experiments were carried out under the following conditions: 20 bar total pressure, a hydrogen/hydrocarbon molar ratio of 8.5, a reaction time of 16 hours (h) per temperature, and a weight hourly space velocity (WHSV) of 10 $h^{-1}$. After the testing at each temperature the zeolitic catalysts were kept at that temperature and under $H_2$ atmosphere for an additional 10 hours. Each zeolitic catalyst sample was prepared to a particle size of 0.2 to 0.4 millimeters (mm). The tested zeolitic samples included Re/Beta>>ZSM-5 (80:20 Beta:ZSM-5 with 0.5 wt. % rhenium), Re/Beta>ZSM-5 (60:40 Beta:ZSM-5 with 0.5 wt. % rhenium), Re/Beta<ZSM-5 (40:60 Beta:ZSM-5 with 0.5 wt. % rhenium), Re/Beta+Re/ZSM-5 (60% Beta with 0.5 wt. % rhenium and 40% ZSM-5 with 0.5 wt. % rhenium physically mixed, each synthesized in accordance with the present disclosure), and AC-140. AC-140 is a commercially available heavy reformate conversion catalyst based on a physical mixture of Beta and ZSM-5 zeolites and serves as a comparative example for the composite zeolite catalysts synthesized in accordance with the present disclosure. The specific formulation is a physical mixture of 60 wt. % of Beta impregnated with 0.1 wt. % Pt and 1 wt. % Ni, 20 wt. % ZSM-5 (metal free), and 20 wt. % of $Al_2O_3$ impregnated with 1 wt. % Ce. The XRD of AC-140 is provided as FIG. 1B with the two distinct peaks for Beta and four distinct peaks for ZSM-5 from FIG. 1A transferred. Each fixed-bed microreactor reactor was prepared with 125 mg of the zeolitic catalyst sample and diluted with silicon carbide (SiC) to a total bed volume of 2.0 ml for testing. The experiments were performed on the same zeolite weight basis so the matrix in the AC-140 was excluded from calculation of the 125 mg. Prior to commencing the catalytic test, the catalyst was reduced in situ at 450° C. for 1 h under $H_2$ flow (50 ml/min) at atmospheric pressure. Four consecutive reactions phases were completed at temperatures of 350° C., 375° C., 400° C., and a return to 350° C.

The reaction products from each of the fixed-bed microreactors were analyzed by on-line gas chromatography using two independent channels (Bruker 450 Gas Chromatograph). Argon (Ar) as an internal standard, $H_2$, methane, and ethane were analyzed in a first channel equipped with a thermal conductivity detector (TCD) and three columns. The three columns were a Hayesep N pre-column (0.5 m length) (Hayes Separations, Inc.), a Hayesep Q (1.5 m length) (Hayes Separations, Inc.), and a 13× molecular sieve (1.2 m length). In a second channel the $C_1$-$C_4$ hydrocarbons were first separated from the aromatics in a CP-Wax capillary column (5.0 m length and 0.32 mm inner diameter) (Cole-Parmer). Subsequently, the $C_1$-$C_4$ gases were separated in a column with CP-PoraBOND Q (25 m length and 0.32 mm inner diameter) (Cole-Parmer) and detected in a flame ionization detector (FID). Separation of the aromatics was completed in a second CP-Wax (1.0 m length and 0.32 mm inner diameter) connected to a second FID.

Figure 4:
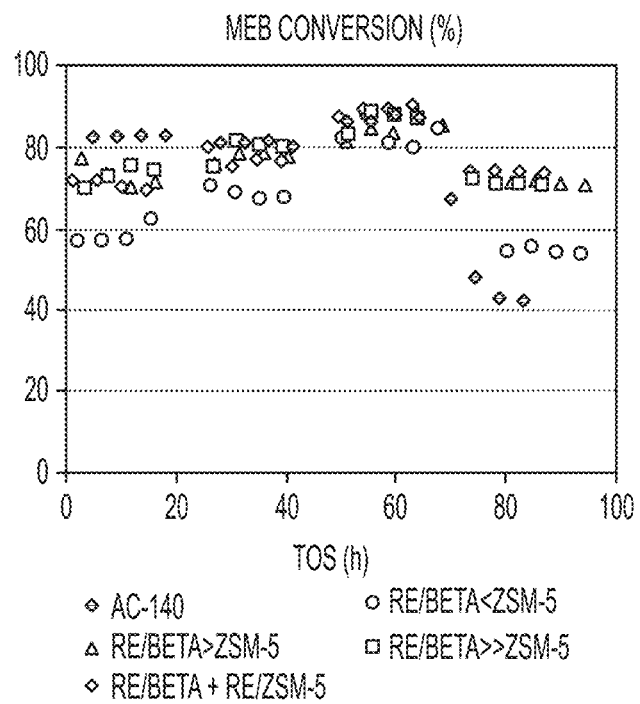
FIG. 4 is a graph of Methylethylbenzene (MEB) conversion of a simulated heavy reformate stream obtained with composite zeolite catalysts synthesized in accordance with one or more embodiments of the present disclosure.
Figure 5:
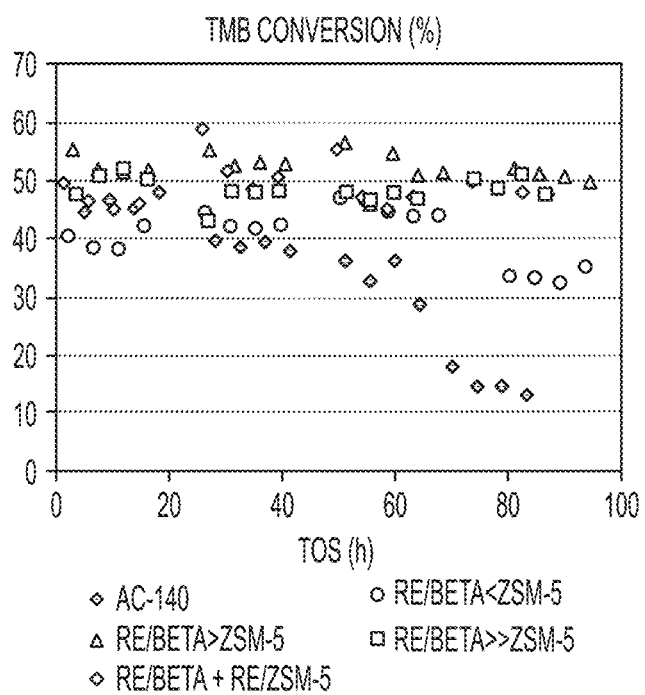
FIG. 5 is a graph of Trimethylbenzene (TMB) conversion of a simulated heavy reformate stream obtained with composite zeolite catalysts synthesized in accordance with one or more embodiments of the present disclosure.
Figure 6:
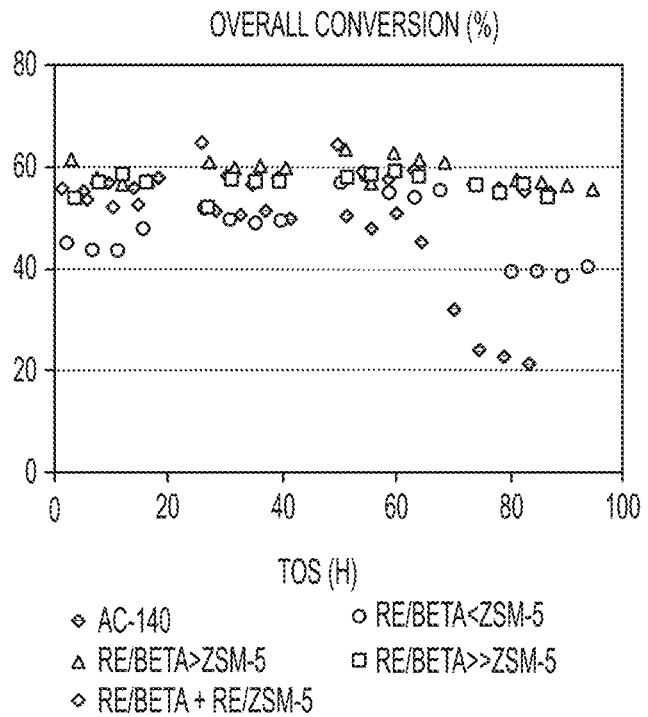
FIG. 6 is a graph of overall conversion (MEB+TMB) of a simulated heavy reformate stream obtained with composite zeolite catalysts synthesized in accordance with one or more embodiments of the present disclosure.
Figure 7:
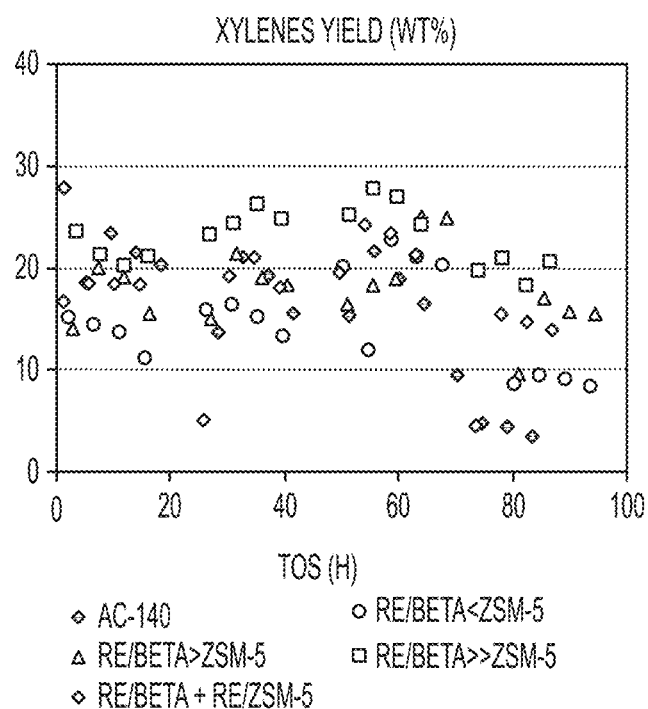
FIG. 7 is a graph of xylenes yield from a simulated heavy reformate stream obtained with composite zeolite catalysts synthesized in accordance with one or more embodiments of the present disclosure.
Figure 8:
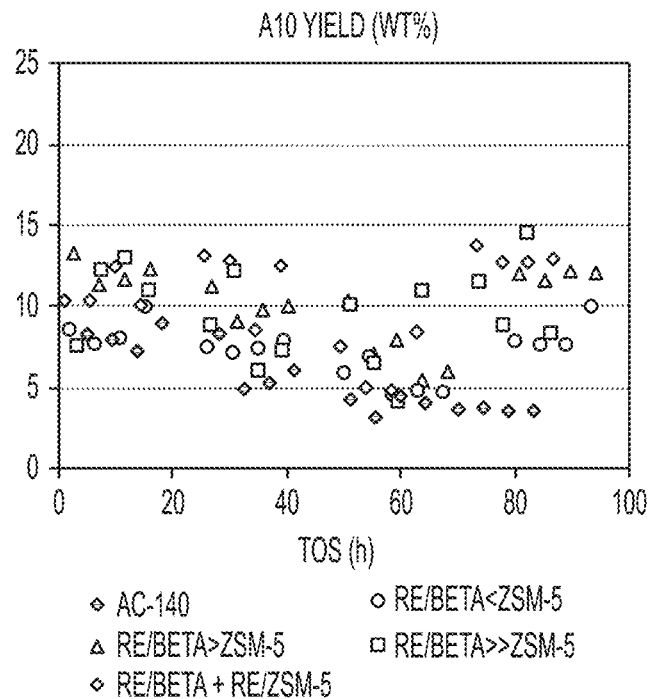
FIG. 8 is a graph of $A_{10}$ yield (yield of aromatics with 10 carbons) from a simulated heavy reformate stream obtained with composite zeolite catalysts synthesized in accordance with one or more embodiments of the present disclosure.
Figure 9:
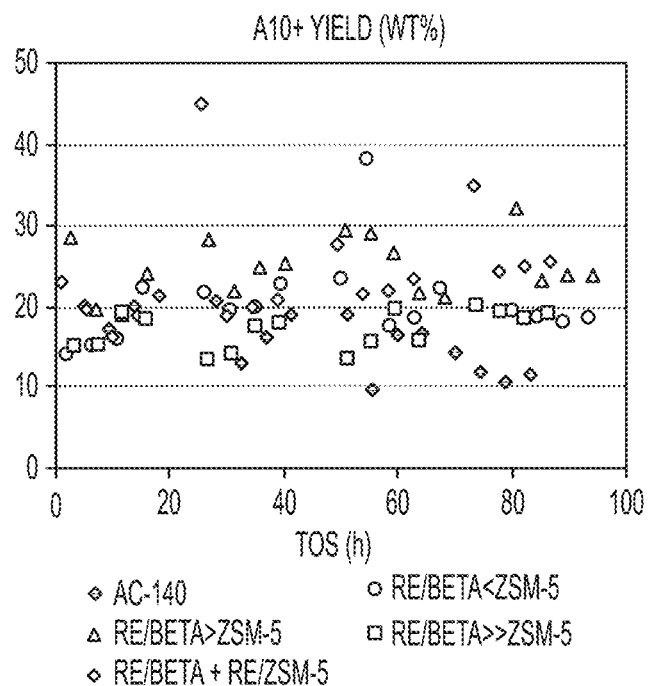
FIG. 9 is a graph of $A_{10+}$ yield (yield of aromatics with more than 10 carbons) from a simulated heavy reformate stream obtained with composite zeolite catalysts synthesized in accordance with one or more embodiments of the present disclosure.
Figure 10:
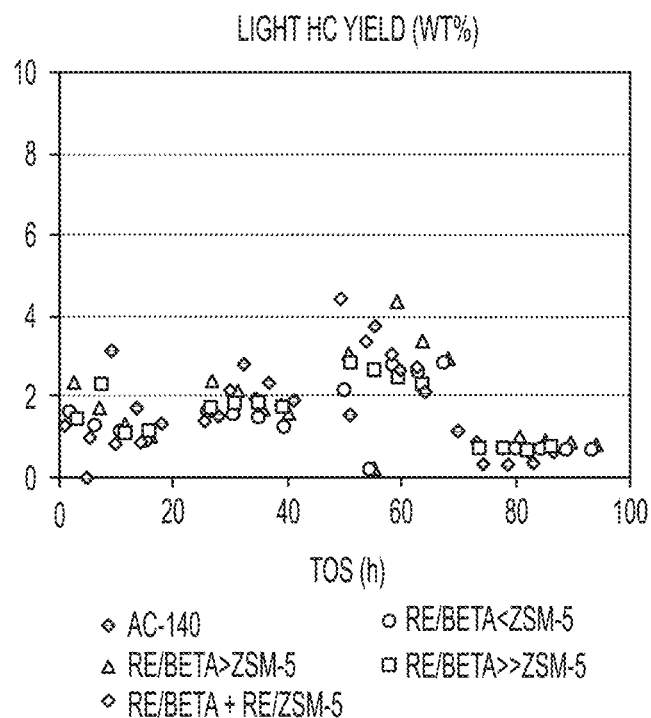
FIG. 10 is a graph of light hydrocarbon yield from a simulated heavy reformate stream obtained with composite zeolite catalysts synthesized in accordance with one or more embodiments of the present disclosure.
Figure 11:
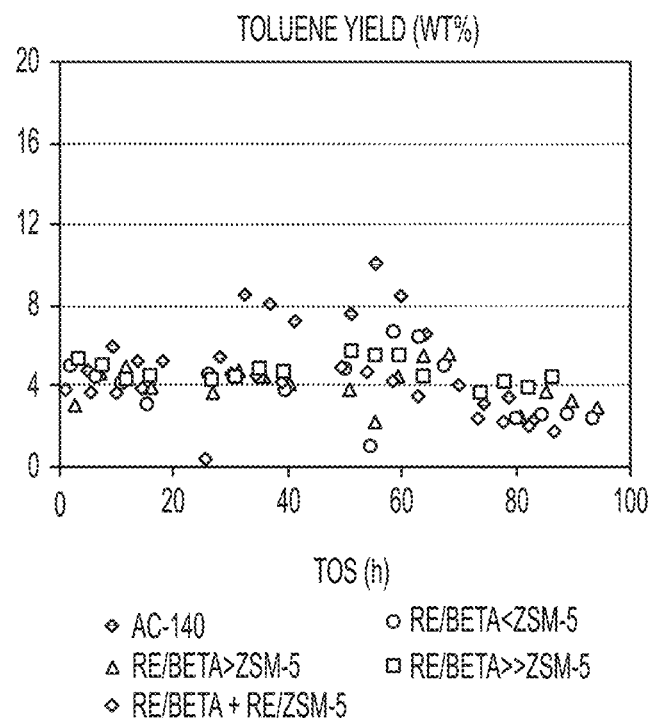
FIG. 11 is a graph of toluene yield from of a simulated heavy reformate stream obtained with composite zeolite catalysts synthesized in accordance with one or more embodiments of the present disclosure.
Figure 12:
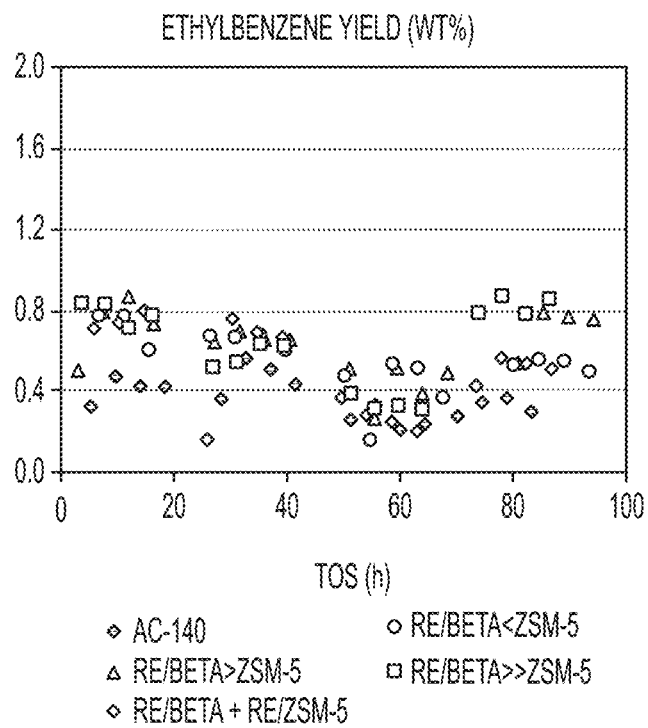
FIG. 12 is a graph of ethylbenzene yield from a simulated heavy reformate stream obtained with composite zeolite catalysts synthesized in accordance with one or more embodiments of the present disclosure.
Figure 13:
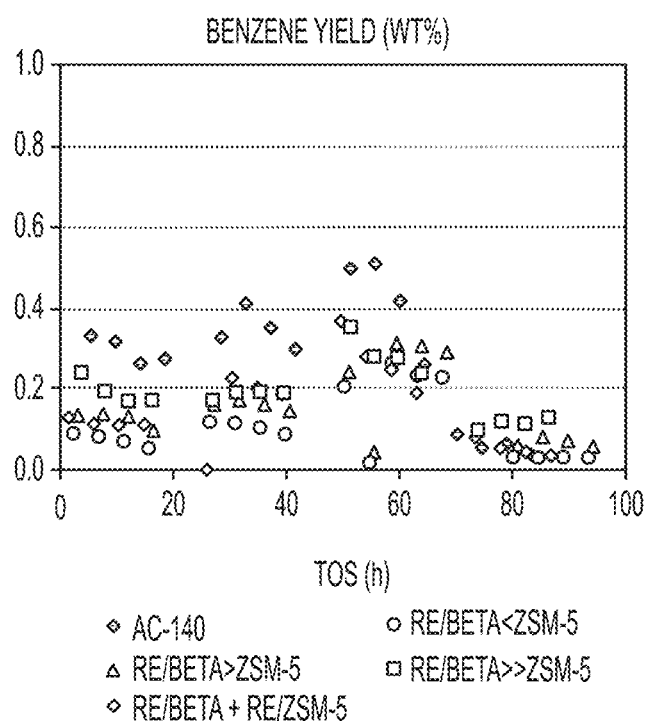
FIG. 13 is a graph of benzene yield from a simulated heavy reformate stream obtained with composite zeolite catalysts synthesized in accordance with one or more embodiments of the present disclosure.

With reference to FIGS. 4, 5 and 6, the MEB conversion (dealkylation), TMB conversion (transalkylation), and overall conversion (MEB+TMB) are illustrated for each of the 5 sample types versus time on stream (TOS). It is noted that the physical mixture of pure Beta and pure ZSM-5, and composite zeolite catalysts (80:20, 60:40, and 40:60 weight ratios of Beta:ZSM-5) each did not exhibit deactivation during the tested TOS when synthesized in accordance with the present disclosure. The lack of deactivation was observed independent of whether the Beta and ZSM-5 were formed simultaneously (for example, Re/Beta>ZSM-5) or pure Beta and ZSM-5 were synthesized individually in accordance with the present disclosure and physically mixed (Re/Beta+Re/ZSM-5). This phenomenon is indicated by the conversion percentage for the initial 350° C. stage at the beginning of each test and the final 350° C. stage at the conclusion of each test being similar. Conversely, as illustrated in FIG. 6, the AC-140 exhibits a deactivation with TOS phenomenon as indicated by the substantially lower conversion percentage during the final 350° C. stage when compared to the initial 350° C. stage. The samples with a larger proportion of the Beta component (Re/Beta>>ZSM-5, Re/Beta>ZSM-5, Re/Beta+Re/ZSM-5) are more active than Re/Beta<ZSM-5, and their activity is comparable or even higher than that of AC-140, especially upon return to 350° C. Without wishing to be bound by theory, this is believed to result because Re/Beta>ZSM-5 and Re/Beta>>ZSM-5, have more Brønsted acid sites than AC-140 and Re/Beta<ZSM-5.

The lower deactivation observed for the composite zeolite catalyst is believed to be due to their higher catalytic efficiency, which reduces the formation of heavy alkylaromatics. The proximity of the two zeolite phases, ZSM-5 and Beta, allows the TMB present in the feed to preferentially react on the Beta crystals with the toluene previously formed by dealkylation of MEB on the ZSM-5 crystals. When the ZSM-5 and Beta zeolite crystals are not so intimately mixed as in the physically mixed catalyst, TMB may react with other TMB by transalkylation to tetramethylbenzene or heavier compounds. Additionally, the small crystal size of ZSM-5 and Beta creates short diffusion pathways which allow the products to diffuse out of the zeolite crystals before undergoing reactions into heavier aromatics, coke precursors, or both. This reduced formation of $A_{10}+$ and coke precursors leads to improved catalyst life.

With reference to FIGS. 7, 8, 9, 10, 11, and 13, the xylenes yield, $A_{10}$ yield, $A_{10+}$ yield, light hydrocarbon yield, toluene yield, ethylbenzene yield, and benzene yield are respectively illustrated for each of the 5 sample types versus TOS. It is noted that Re/Beta>>ZSM-5 favors the xylenes production as compared to the rest of the catalysts. Without wishing to be bound by theory, it is believed Re/Beta<ZSM-5 produces less xylenes than the catalysts with a higher Beta proportion due to its lower activity as compared to the other samples. Additionally, it is believed Re/Beta<ZSM-5 produces less xylenes than the catalysts with a higher Beta proportion because the larger proportion of ZSM-5 favors MEB dealkylation, but reduces the transalkylation capacity of the composite catalyst.

The results generated from testing the samples with the simulated heavy reformate provided information regarding the relative activity of the different catalyst compositions and their stability towards deactivation with an extended TOS. The catalysts were also tested under conditions closer to industrial conditions which would be observed for conversion of heavy reformate to xylenes. To more accurately reflect industrial conditions a supply of actual industrial heavy reformate with known composition was utilized. Table 4 provided infra delineates the composition of the industrial heavy reformate used for testing and Table 5 provides the relative ratios of various components.

TABLE 4

Industrial Heavy Reformate Composition

| Hydrocarbon Type | Hydrocarbon Sub-Type | | Mass % |
|---|---|---|---|
| $A_8$ | Total | | 3.94 |
| | Ethylbenzene | | 0.03 |
| | p-xylene | | 0.15 |
| | m-xylene | | 0.38 |
| | o-xylene | | 3.38 |
| $A_9$ | Total | | 82.75 |
| | Isopropylbenzene | Total | 0.43 |
| | n-propylbenzene | Total | 2.07 |
| | Methylethylbenzene | Total | 19.62 |
| | (MEB) | m- and p-MEB | 15.33 |
| | | o-MEB | 4.29 |
| | Trimethylbenzene | Total | 60.63 |
| | (TMB) | 1,3,5-TMB | 11.69 |
| | | 1,2,4-TMB | 40.81 |
| | | 1,2,3-TMB | 8.13 |
| $A_{10+}$ | Total | | 13.33 |

TABLE 5

Industrial Heavy Reformate Composition Ratio

| $A_8$ | Ethylbenzene:Total $A_8$ | 0.0076 |
|---|---|---|
| | p-xylene:Total $A_8$ | 0.038 |
| | m-xylene:Total $A_8$ | 0.096 |
| | o-xylene:Total $A_8$ | 0.858 |
| $A_9$ | Isopropylbenzene:Total $A_9$ | 0.0052 |
| | n-propylbenzene:Total $A_9$ | 0.025 |
| | Total Methylethylbenzene (MEB):Total $A_9$ | 0.237 |
| | m- and p-MEB:Total $A_9$ | 0.185 |
| | o-MEB:Total $A_9$ | 0.052 |
| | m- and p-MEB:Total MEB | 0.781 |
| | o-MEB:Total MEB | 0.219 |
| | Total Trimethylbenzene (TMB):Total $A_9$ | 0.733 |
| | 1,3,5-TMB:Total $A_9$ | 0.141 |
| | 1,2,4-TMB:Total $A_9$ | 0.493 |

TABLE 5-continued

Industrial Heavy Reformate Composition Ratio

| 1,2,3-TMB:Total $A_9$ | 0.098 |
|---|---|
| 1,3,5-TMB:Total TMB | 0.193 |
| 1,2,4-TMB:Total TMB | 0.673 |
| 1,2,3-TMB:Total TMB | 0.124 |
| Total $A_9$:Total $A_{10+}$ | 6.21 |

Catalytic test for conversion of the industrial heavy reformate feed were performed in a fixed-bed stainless-steel tubular reactor. The reactor had a 10.5 mm internal diameter and a 20 centimeter (cm) length. The catalytic experiments in the fixed-bed tubular reactor were carried out under the following conditions: 20 bar total pressure, a hydrogen/hydrocarbon molar ratio of 4:1 and a weight hourly space velocity (WHSV) of 10 $h^{-1}$. The reactor was charged with 0.75 grams (g) of catalyst with a particle size of 0.2 to 0.4 mm for each test. The tested zeolitic samples included Re/Beta>>ZSM-5 (80:20 Beta:ZSM-5 with 0.5 wt. % rhenium), Re/Beta>ZSM-5 (60:40 Beta:ZSM-5 with 0.5 wt. % rhenium), Re/Beta<ZSM-5 (40:60 Beta:ZSM-5 with 0.5 wt. % rhenium), Re/Beta+Re/ZSM-5 (60% Beta with 0.5 wt. % rhenium and 40% ZSM-5 with 0.5 wt. % rhenium physically mixed, each synthesized in accordance with the present disclosure), and AC-140. The catalyst was diluted with SiC to bring the total volume up to a total bed volume of 5.0 ml. For the AC-140 sample, the amount of catalyst added was adjusted according to its zeolite content in order to have 0.75 g of zeolite (the matrix was excluded). Gaseous compounds ($H_2$, $N_2$) were fed into the system by mass flow meters via a vaporizer. Nitrogen was also fed into the system as an internal reference. The industrial heavy reformate was fed by means of a high performance liquid chromatography (HPLC) pump to the vaporizer. The vaporizer was operated at 300° C. and provided a steady and non-pulsing flow of reactants to the reactor. Prior to commencing the catalytic test, the catalyst was reduced in situ at 450° C. for 1 h under $H_2$ flow (50 ml/min) at atmospheric pressure. For the catalytic testing, four consecutive reactions phases were completed at temperatures of 350° C. (7 h), 375° C. (5 h), 400° C. (5 h), and a return to 350° C. (5 h).

During reaction, the effluent stream was analyzed on-line at intervals of 32 min in a Varian CP3800 equipped with two detection channels. The first channel was equipped with a TCD, and allowed separation, identification and quantification of permanent gases and light hydrocarbons ($C_1$-$C_5$). The heavier hydrocarbons ($C_{6+}$) were separated in a WAX capillary column (60 m length, 0.2 mm inner diameter) and detected by a FID. A Wax capillary column is a capillary column where polyethylene glycols are used as the stationary phase and is specially indicated for separation of aromatic compounds. Nitrogen was employed as an internal reference allowing an accurate quantification of the amount and distribution of reaction products.

Figure 14:
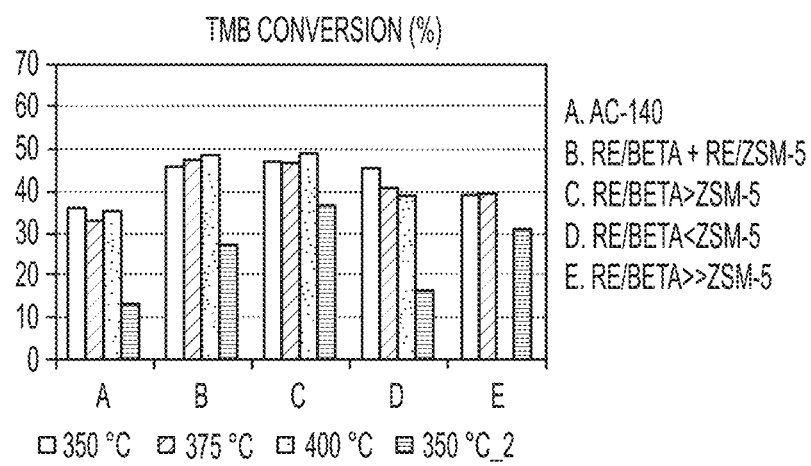
FIG. 14 is a graph of TMB conversion of an industrial heavy reformate stream obtained with composite zeolite catalysts synthesized in accordance with one or more embodiments of the present disclosure.
Figure 15:
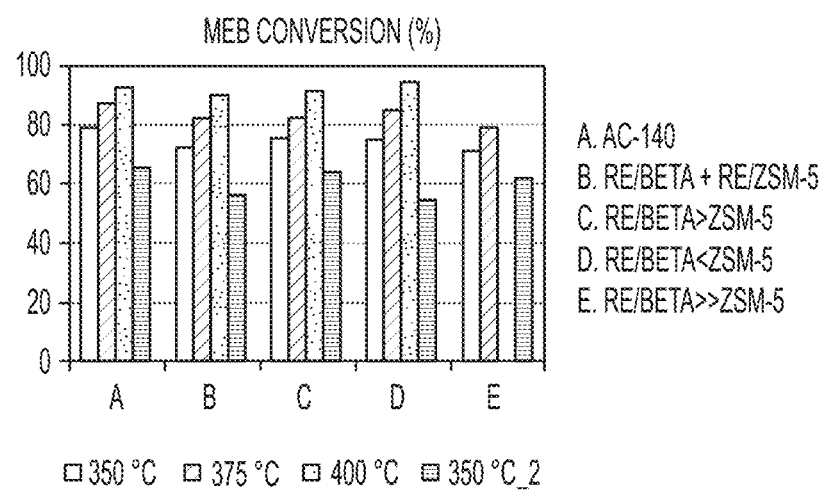
FIG. 15 is a graph of MEB conversion of an industrial heavy reformate stream obtained with composite zeolite catalysts synthesized in accordance with one or more embodiments of the present disclosure.
Figure 16:
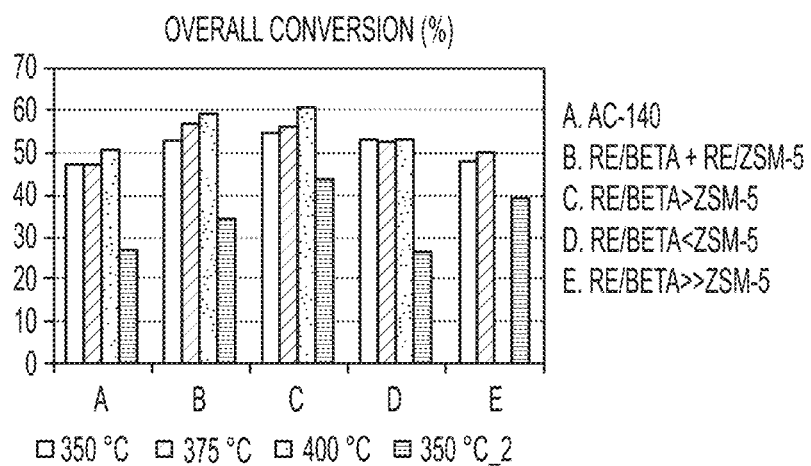
FIG. 16 is a graph of overall conversion of an industrial heavy reformate stream obtained with composite zeolite catalysts synthesized in accordance with one or more embodiments of the present disclosure.
Figure 17:
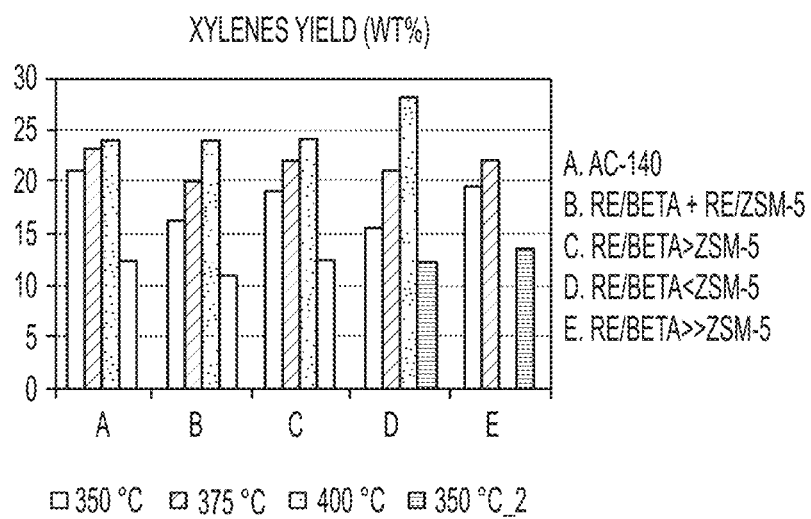
FIG. 17 is a graph of xylenes yield from an industrial heavy reformate stream obtained with composite zeolite catalysts synthesized in accordance with one or more embodiments of the present disclosure.
Figure 18:
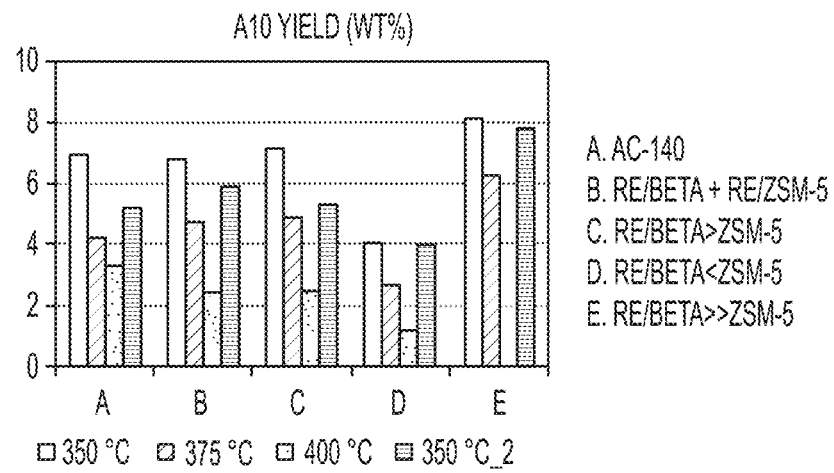
FIG. 18 is a graph of $A_{10}$ yield from an industrial heavy reformate stream obtained with composite zeolite catalysts synthesized in accordance with one or more embodiments of the present disclosure.
Figure 19:
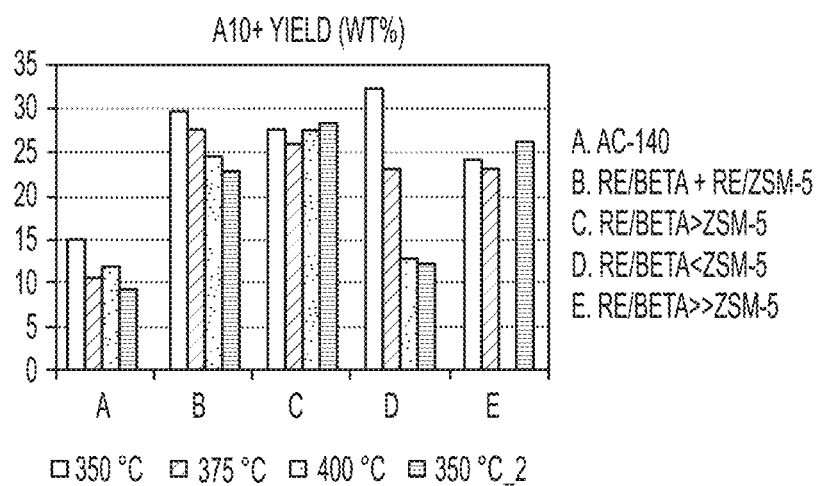
FIG. 19 is a graph of $A_{10+}$ yield from an industrial heavy reformate stream obtained with composite zeolite catalysts synthesized in accordance with one or more embodiments of the present disclosure.
Figure 20:
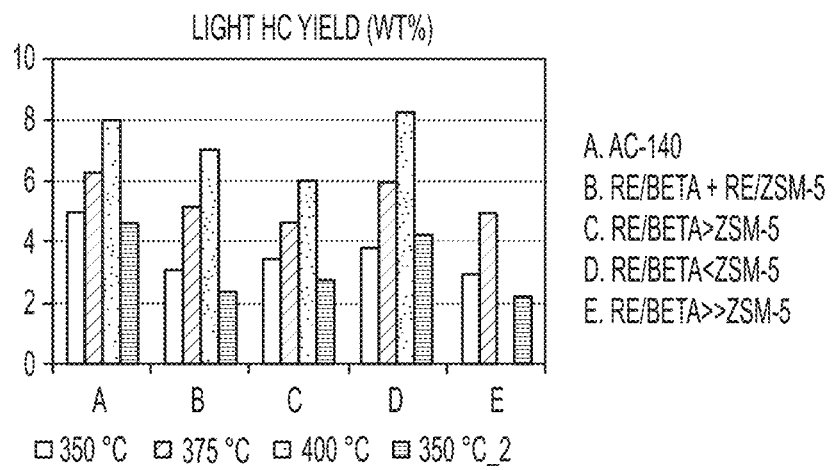
FIG. 20 is a graph of light hydrocarbon yield from an industrial heavy reformate stream obtained with composite zeolite catalysts synthesized in accordance with one or more embodiments of the present disclosure.
Figure 21:
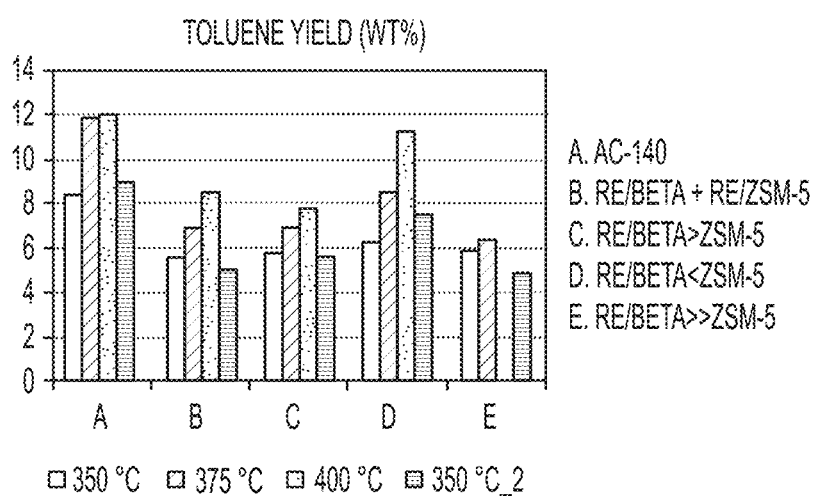
FIG. 21 is a graph of toluene yield from of an industrial heavy reformate stream obtained with composite zeolite catalysts synthesized in accordance with one or more embodiments of the present disclosure.
Figure 22:
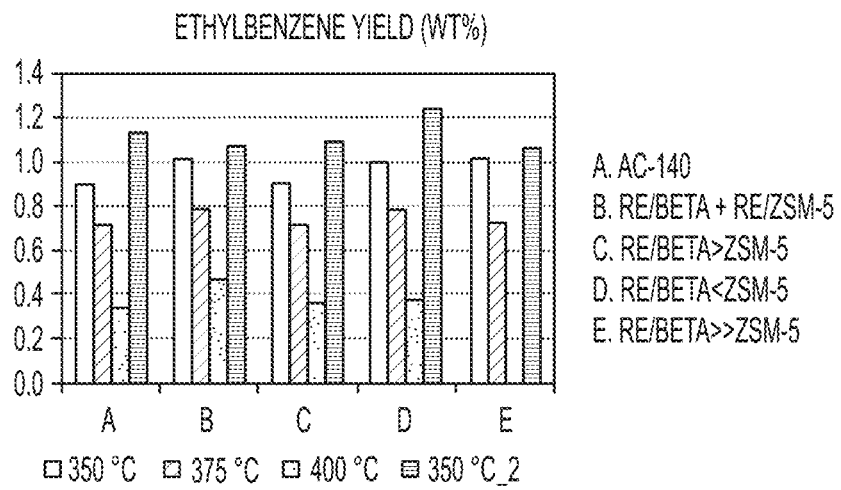
FIG. 22 is a graph of ethylbenzene yield from an industrial heavy reformate stream obtained with composite zeolite catalysts synthesized in accordance with one or more embodiments of the present disclosure.
Figure 23:
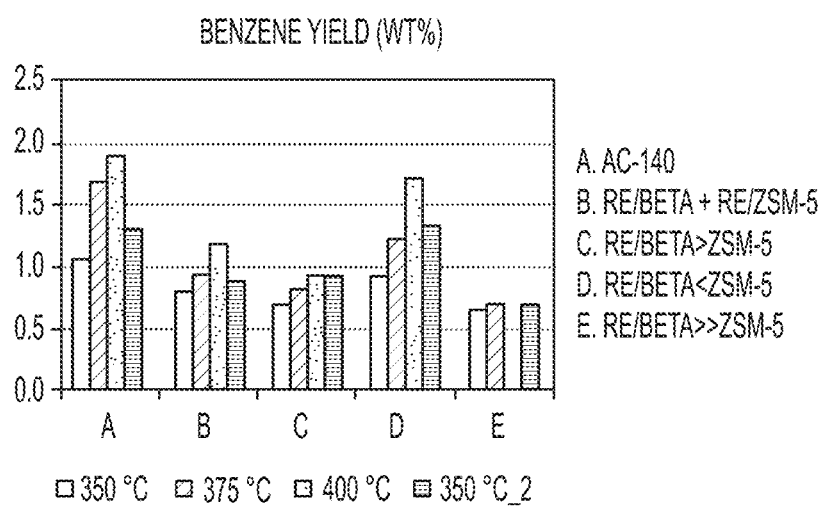
FIG. 23 is a graph of benzene yield from an industrial heavy reformate stream obtained with composite zeolite catalysts synthesized in accordance with one or more embodiments of the present disclosure.

With reference to FIGS. 14, 15 and 16, the TMB conversion (transalkylation), MEB conversion (dealkylation), and overall conversion (MEB+TMB) are respectively illustrated for each of the 5 sample types versus time on stream (TOS). It is noted that Re/Beta>ZSM-5 indicated more activity than the physical mixture of the pure Re/Beta and pure Re/ZSM-5 in the same proportion (Re/Beta+Re/ZSM-5). Specifically, the Re/Beta>ZSM-5 has overall conversion percentages of 54.3, 55.8, 60.4, and 43.6 for temperatures of 350° C., 375° C., 400° C., and a return to 350° C. respectively compared to overall conversion percentages of 52.4, 56.4, 59.2, and 34.4 respectively for Re/Beta+Re/ZSM-5. The individual TMB conversion percentages and MEB conversion percentages are provided in Table 6. It is also noted that larger ratios of the ZSM-5 component provides higher MEB conversion because ZSM-5 favors the dealkylation reaction while larger Beta content results in catalysts more active for the TMB conversion. The values for each conversion are provided in Table 6.

TABLE 6

TMB, MEB, and Overall Conversion

| Catalyst | Temperature | TMB Conversion (%) | MEB Conversion (%) | Overall Conversion (%) |
|---|---|---|---|---|
| AC-140 | 350° C. | 35.51 | 78.58 | 46.89 |
|  | 375° C. | 32.79 | 87.01 | 47.11 |
|  | 400° C. | 35.19 | 92.95 | 50.45 |
|  | 350° C. (Return) | 12.66 | 65.48 | 26.62 |
| Re/Beta + Re/ZSM-5 | 350° C. | 45.40 | 71.93 | 52.41 |
|  | 375° C. | 47.35 | 81.59 | 56.40 |
|  | 400° C. | 48.38 | 89.40 | 59.22 |
|  | 350° C. (Return) | 26.65 | 56.00 | 34.40 |
| Re/Beta > ZSM-5 | 350° C. | 46.71 | 75.46 | 54.31 |
|  | 375° C. | 46.40 | 82.10 | 55.83 |
|  | 400° C. | 49.19 | 91.49 | 60.37 |
|  | 350° C. (Return) | 36.24 | 63.90 | 43.55 |
| Re/Beta < ZSM-5 | 350° C. | 45.01 | 75.05 | 52.95 |
|  | 375° C. | 40.74 | 84.99 | 52.43 |
|  | 400° C. | 38.60 | 93.93 | 53.22 |
|  | 350° C. (Return) | 16.47 | 54.17 | 26.43 |
| Re/Beta >> ZSM-5 | 350° C. | 38.81 | 70.55 | 47.57 |
|  | 375° C. | 38.88 | 78.68 | 49.87 |
|  | 350° C. (Return) | 30.68 | 61.63 | 39.22 |

With reference to FIGS. 17, 18, 19, 20, 21, 22, and 23, the xylenes yield, $A_{10}$ yield, $A_{10+}$ yield light hydrocarbon yield, toluene yield, ethylbenzene yield, and benzene yield are respectively illustrated for each of the 5 sample types versus TOS. It is noted that Re/Beta>ZSM-5 favors the xylenes production as compared to the physical mixture of the pure Re/Beta and pure Re/ZSM-5 physically mixed in the same proportion (Re/Beta+Re/ZSM-5) and similarly produces a lesser amount of light hydrocarbons. The same is illustrated when compared to AC-140. The numerical values of the yield as a wt. % for each species utilizing each catalyst is provided in Table 7. This improvement in xylenes production illustrates the benefit of synthesis according to the methods of the present disclosure where the Beta and ZSM-5 are in intimate contact opposed to physically mixing Beta and ZSM-5 after formation. An additional advantage is that the active multizeolite phase, containing ZSM-5 and Beta zeolites, is obtained in a single step one-pot synthesis.

TABLE 7

Product Yields

| Catalyst | Temperature | Xylenes Yield (wt. %) | $A_{10}$ Yield (wt. %) | $A_{10+}$ Yield (wt. %) | Light HC Yield (wt. %) | Toluene Yield (wt. %) | Ethylbenzene Yield (wt. %) | Benzene Yield (wt. %) |
|---|---|---|---|---|---|---|---|---|
| AC-140 | 350° C. | 20.94 | 6.91 | 15.08 | 4.96 | 8.34 | 0.90 | 1.08 |
|  | 375° C. | 23.28 | 4.20 | 10.49 | 6.16 | 11.83 | 0.71 | 1.69 |
|  | 400° C. | 23.96 | 3.30 | 11.59 | 7.91 | 12.01 | 0.34 | 1.91 |
|  | 350° C. (Return) | 12.36 | 5.13 | 9.06 | 4.58 | 9.00 | 1.13 | 1.33 |
| Re/Beta + Re/ZSM-5 | 350° C. | 16.28 | 6.69 | 29.25 | 3.10 | 5.60 | 1.01 | 0.80 |
|  | 375° C. | 20.27 | 4.74 | 27.09 | 5.08 | 6.84 | 0.78 | 0.95 |
|  | 400° C. | 24.09 | 2.40 | 24.23 | 6.97 | 8.44 | 0.47 | 1.20 |
|  | 350° C. (Return) | 11.01 | 5.89 | 22.39 | 2.43 | 5.01 | 1.07 | 0.89 |
| Re/Beta > ZSM-5 | 350° C. | 19.13 | 7.06 | 27.35 | 3.40 | 5.79 | 0.90 | 0.69 |
|  | 375° C. | 22.05 | 4.85 | 25.52 | 4.62 | 6.87 | 0.72 | 0.83 |
|  | 400° C. | 24.13 | 2.43 | 27.30 | 6.03 | 7.78 | 0.36 | 0.94 |
|  | 350° C. (Return) | 12.46 | 5.26 | 27.77 | 2.76 | 5.61 | 1.09 | 0.93 |
| Re/Beta < ZSM-5 | 350° C. | 15.46 | 4.04 | 31.77 | 3.78 | 6.21 | 1.00 | 0.95 |
|  | 375° C. | 21.00 | 2.68 | 22.62 | 5.93 | 8.51 | 0.79 | 1.25 |
|  | 400° C. | 28.22 | 1.12 | 12.57 | 8.14 | 11.23 | 0.37 | 1.72 |
|  | 350° C. (Return) | 12.18 | 4.02 | 12.05 | 4.22 | 7.47 | 1.24 | 1.34 |
| Re/Beta>>ZSM-5 | 350° C. | 19.76 | 8.08 | 23.74 | 2.96 | 5.89 | 1.01 | 0.67 |
|  | 375° C. | 22.17 | 6.16 | 22.58 | 4.95 | 6.41 | 0.72 | 0.72 |
|  | 350° C. (Return) | 13.60 | 7.73 | 25.79 | 2.22 | 4.84 | 1.07 | 0.70 |

It should be understood that the various aspects of the composite zeolite catalyst, the method of making the same, the method of making xylene using the same, and a system for making xylene using the same are described and such aspects may be utilized in conjunction with various other aspects.

In a first aspect, the disclosure provides a method of forming a composite zeolite catalyst. The method comprises combining a silicon source and an aqueous organic structure directing agent to form a silica intermediary gel. The aqueous organic directing structure agent comprises a polyamino cation compound. The method further comprises introducing an aluminum precursor to the silica intermediary gel to form a catalyst precursor gel and evaporating the water in the catalyst precursor gel to form a catalyst gel. The method additionally comprises heating the catalyst gel to form a composite zeolite catalyst particle. The composite zeolite catalyst particle has both Beta and ZSM-5 zeolites and is characterized by having an intergrowth region with a mixture of both Beta crystals and ZSM-5 crystals.

In a second aspect, the disclosure provides a method of forming a composite zeolite catalyst of the first aspect in which the silicon source comprises a silica gel, silicon oxide, silicon halide, tetraalkyl orthosilicate, silicate, silicic acid, fumed silica, sodium silicate, colloidal silica, a previously synthesized crystalline material, a previously synthesized amorphous material, or combinations thereof.

In a third aspect, the disclosure provides a method of forming a composite zeolite catalyst of the first or second aspect in which the silicon source is a silica gel.

In a fourth aspect, the disclosure provides a method of forming a composite zeolite catalyst of the third aspect in which the silica gel is a 20 to 60 wt. % suspension of silica in water.

In a fifth aspect, the disclosure provides a method of forming a composite zeolite catalyst of any of the first through fourth aspects in which the polyamino cation comprises a structure in accordance with:

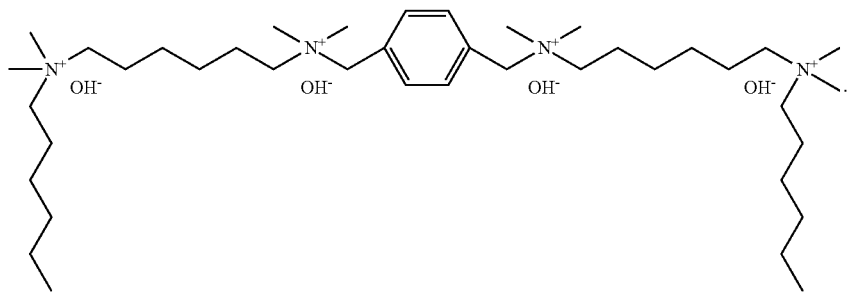

In a sixth aspect, the disclosure provides a method of forming a composite zeolite catalyst of any of the first through fifth aspects in which the aqueous organic directing structure comprises from 5 to 15 wt. % polyamino cation and from 85 to 95 wt. % water.

In a seventh aspect, the disclosure provides a method of forming a composite zeolite catalyst of any of the first through sixth aspects in which the aluminum precursor is an alumina ($Al_2O_3$), aluminum hydroxide ($Al(OH)_3$), aluminum oxide hydroxide (AlO(OH)) (also called boehmite), or combinations thereof.

In an eighth aspect, the disclosure provides a method of forming a composite zeolite catalyst of any of the first through seventh aspects in which the aluminum precursor is aluminum oxide hydroxide (AlO(OH)) (also called boehmite).

In a ninth aspect, the disclosure provides a method of forming a composite zeolite catalyst of any of the first through eighth aspects in which the heating of the catalyst gel is conducted in a sealed vessel under autogenous pressure at a temperature from 130 to 180° C. with stirring.

In a tenth aspect, the disclosure provides a method of forming a composite zeolite catalyst of any of the first through ninth aspects in which the heating is continued for 4-10 days.

In an eleventh aspect, the disclosure provides a method of forming a composite zeolite catalyst of any of the first through tenth aspects in which the method further comprises impregnating the composite zeolite catalyst with up to 20 wt. % of one or more metals selected from the group consisting of molybdenum, chromium, platinum, nickel, tungsten, palladium, ruthenium, gold, rhenium, rhodium, or combinations thereof and their respective oxides to yield impregnated composite zeolite catalyst.

In a twelfth aspect, the disclosure provides a method of forming a composite zeolite catalyst of the eleventh aspect in which the metal comprises rhenium or a rhenium oxide.

In a thirteenth aspect, the disclosure provides a composite zeolite catalyst. The composite zeolite catalyst comprises ZSM-5 and Beta within a single catalyst particle. The composite zeolite catalyst has an intergrowth region with a mixture of Beta crystals and ZSM-5 crystals, the intergrowth of ZSM-5 and Beta characterized by an XRD curve having signature peaks at 7.6±0.2, 7.9±0.2, 8.8±0.2, 22.4±0.2, 23.1±0.2 and 23.9±0.2.

In a fourteenth aspect, the disclosure provides a composite zeolite catalyst of the thirteenth aspect in which the composite zeolite catalyst further comprises one or more metals or metal oxides impregnated into the composite zeolite catalyst.

In a fifteenth aspect, the disclosure provides a composite zeolite catalyst of the thirteenth or fourteenth aspects in which the composite zeolite catalyst further comprises up to 20 wt. % of one or more metals selected from the group consisting of molybdenum, chromium, platinum, nickel, tungsten, palladium, ruthenium, gold, rhenium, rhodium, or combinations thereof and their respective oxides to yield impregnated zeolite catalyst.

In a sixteenth aspect, the disclosure provides a method of making xylene. The method comprises feeding heavy reformate to a reactor and producing xylene by simultaneously performing dealkylation and transalkylation of the heavy reformate in the reactor. The reactor contains a composite zeolite catalyst comprising a plurality of catalyst particles, where each catalyst particle comprises both ZSM-5 and Beta zeolites and has an intergrowth region with a mixture of both Beta crystals and ZSM-5 crystals. Each composite zeolite catalyst particle is able to simultaneously catalyze both the dealkylation and transalkylation reactions.

In a seventeenth aspect, the disclosure provides a method of making xylene of the sixteenth aspect in which the heavy reformate comprises at least 15 wt. % methylethylbenzene (MEB) and at least 50 wt. % trimethylbenzene (TMB).

In an eighteenth aspect, the disclosure provides a method of making xylene of the sixteenth or seventeenth aspects in which the reactor is operated at 300° C. to 450° C.

In a nineteenth aspect, the disclosure provides a method of making xylene of any of the sixteenth through eighteenth aspects in which the composite zeolite catalyst achieves a greater TMB conversion as compared to a comparable physical mixture of both ZSM-5 and Beta zeolites at comparable processing conditions.

In an twentieth aspect, the disclosure provides a method of making xylene of any of the sixteenth through nineteenth aspects in which the composite zeolite catalyst achieves a greater MEB conversion as compared to a comparable physical mixture of both ZSM-5 and Beta zeolites at comparable processing conditions.

In a twenty-first aspect, the disclosure provides a method of making xylene of any of the sixteenth through twentieth aspects in which the composite zeolite catalyst achieves a greater xylene yield as compared to a comparable physical mixture of both ZSM-5 and Beta zeolites at comparable processing conditions.

In a twenty-second aspect, the disclosure provides a system for making xylene. The system comprises a reactor. The reactor contains a composite zeolite catalyst comprising a plurality of catalyst particles, where each catalyst particle comprises both ZSM-5 and Beta zeolites and has an intergrowth region with a mixture of both Beta crystals and ZSM-5 crystals.

In a twenty-third aspect, the disclosure provides a system for making xylene of the twenty-second aspect in which the composite zeolite catalyst further comprises one or more metals or metal oxides impregnated into the composite zeolite catalyst.

In a twenty-fourth aspect, the disclosure provides a system for making xylene of the twenty-second or twenty-third aspects in which the composite zeolite catalyst further compromises up to 20 wt. % of one or more metals selected from the group consisting of molybdenum, chromium, platinum, nickel, tungsten, palladium, ruthenium, gold, rhenium, rhodium, or combinations thereof and their respective oxides to yield impregnated composite zeolite catalyst.

In a twenty-fifth aspect, the disclosure provides a system for making xylene of any of the twenty-second through twenty-fourth aspects in which the intergrowth of ZSM-5 and Beta is characterized by an XRD curve having signature peaks at 7.6±0.2, 7.9±0.2, 8.8±0.2, 22.4±0.2, 23.1±0.2 and 23.9±0.2.

It should be apparent to those skilled in the art that various modifications and variations can be made to the described embodiments without departing from the spirit and scope of the claimed subject matter. Thus, it is intended that the specification cover the modifications and variations of the various described embodiments provided such modification and variations come within the scope of the appended claims and their equivalents.

Throughout this disclosure ranges are provided. It is envisioned that each discrete value encompassed by the ranges are also included. Additionally, the ranges which may be formed by each discrete value encompassed by the explicitly disclosed ranges are equally envisioned.

What is claimed is:

1. A method of forming a composite zeolite catalyst, the method comprising:
    combining a silicon source and an aqueous organic structure directing agent to form a silica intermediary gel, where the aqueous organic directing structure agent comprises a polyamino cation compound having a structure in accordance with $N_4$-phe-$C_n(OH)_4$, with "n" varying in the range of 6 to 22;
    introducing an aluminum precursor to the silica intermediary gel to form a catalyst precursor gel;
    evaporating the water in the catalyst precursor gel to form a catalyst gel; and
    heating the catalyst gel to form a composite zeolite catalyst particle, where the catalyst particle has both Beta and ZSM-5 zeolites and is characterized by having an intergrowth region with a mixture of both Beta crystals and ZSM-5 crystals.

2. The method of claim 1 where the silicon source comprises a silica gel, silicon oxide, silicon halide, tetraalkyl orthosilicate, silicate, silicic acid, fumed silica, sodium silicate, colloidal silica, or combinations thereof.

3. The method of claim 1 where the silicon source is a silica gel and the silica gel is a 20 to 60 wt. % suspension of silica in water.

4. The method of claim 1 where the polyamino cation comprises a structure in accordance with:

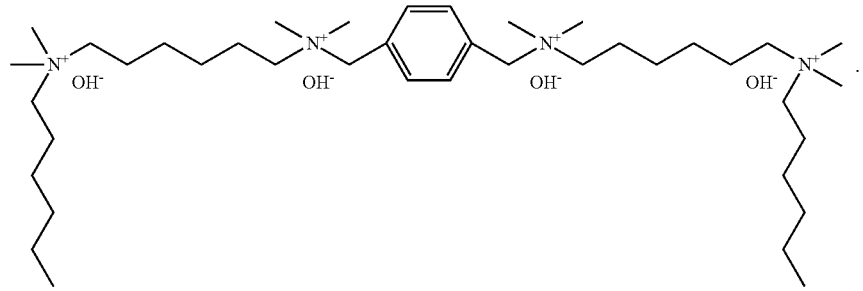

5. The method of claim 1 where the aqueous organic directing structure comprises from 5 to 15 wt. % polyamino cation and from 85 to 95 wt. % water.

6. The method of claim 1 where the aluminum precursor is alumina ($Al_2O_3$), aluminum hydroxide ($Al(OH)_3$), aluminum oxide hydroxide ($AlO(OH)$), or combinations thereof.

7. The method of claim 1 where the heating of the catalyst gel is conducted in a sealed vessel under autogenous pressure at a temperature from 130 to 180° C. with stirring and the heating is continued for 4-10 days.

8. The method of claim 1 where the method further comprises impregnating the composite zeolite catalyst with up to 20 wt. % of one or more metals selected from the group consisting of molybdenum, chromium, platinum, nickel, tungsten, palladium, ruthenium, gold, rhenium, rhodium, or combinations thereof to yield impregnated composite zeolite catalyst.

9. A composite zeolite catalyst,
the composite zeolite catalyst comprises ZSM-5 and Beta within a single catalyst particle,
where the composite zeolite catalyst has an intergrowth region with a mixture of Beta crystals and ZSM-5 crystals, the intergrowth of ZSM-5 and Beta characterized by an XRD curve having signature peaks at 7.6±0.2, 7.9±0.2, 8.8±0.2, 22.4±0.2, 23.1±0.2 and 23.9±0.2 degrees, and where
the composite zeolite catalyst further comprises up to 20 wt. % of one or more metals selected from the group consisting of molybdenum, tungsten, ruthenium, gold, rhenium, rhodium, or combinations thereof to yield impregnated zeolite catalyst.

10. The composite zeolite catalyst of claim 9, where the composite zeolite catalyst further comprises up to 20 wt. % rhenium in the form of ammonium perrhenate, molybdenum in the form of ammonium molybdate tetrahydrate, or combinations thereof to yield impregnated zeolite catalyst.

11. A method of making xylene, the method comprising:
feeding heavy reformate to a reactor, the reactor containing a composite zeolite catalyst comprising a plurality of catalyst particles, where each catalyst particle comprises both ZSM-5 and Beta zeolites and has an intergrowth region with a mixture of both Beta crystals and ZSM-5 crystals; and
producing xylene by simultaneously performing transalkylation and dealkylation of the heavy reformate in the reactor, where each composite zeolite catalyst particle is able to simultaneously catalyze both the transalkylation and dealkylation reactions,
where the composite zeolite catalyst further comprises up to 20 wt. % of one or more metals selected from the group consisting of molybdenum, tungsten, ruthenium, gold, rhenium, rhodium, or combinations thereof to yield impregnated zeolite catalyst.

12. The method of claim 11, where the composite zeolite catalyst further comprises up to 20 wt. % rhenium in the form of ammonium perrhenate, molybdenum in the form of ammonium molybdate tetrahydrate, or combinations thereof to yield impregnated zeolite catalyst.

13. The method of claim 11, where the heavy reformate comprises at least 15 wt. % methylethylbenzene (MEB) and at least 50 wt. % trimethylbenzene (TMB).

14. A system for making xylene, the system comprising:
a reactor, the reactor containing a composite zeolite catalyst comprising a plurality of catalyst particles, where each catalyst particle comprises both ZSM-5 and Beta zeolites and has an intergrowth region with a mixture of both Beta crystals and ZSM-5 crystals, where
the composite zeolite catalyst further comprises up to 20 wt. % of one or more metals selected from the group consisting of molybdenum, tungsten, ruthenium, gold, rhenium, rhodium, or combinations thereof to yield impregnated composite zeolite catalyst.

15. The system of claim 14, where the composite zeolite catalyst further comprises up to 20 wt. % rhenium in the form of ammonium perrhenate, molybdenum in the form of ammonium molybdate tetrahydrate, or combinations thereof to yield impregnated zeolite catalyst.

* * * * *